(12) United States Patent
Kai et al.

(10) Patent No.: US 7,482,339 B2
(45) Date of Patent: Jan. 27, 2009

(54) 2-NAPHTHYLIMINO-1,3-THIAZINE DERIVATIVE

(75) Inventors: Hiroyuki Kai, Osaka (JP); Yasuhide Morioka, Toyonaka (JP); Katsumi Koike, Koka (JP)

(73) Assignee: Shionogi and Co., Ltd., Osaka (JP)

( * ) Notice: Subject to any disclaimer, the term of this patent is extended or adjusted under 35 U.S.C. 154(b) by 362 days.

(21) Appl. No.: 10/568,963

(22) PCT Filed: Aug. 24, 2004

(86) PCT No.: PCT/JP2004/012086

§ 371 (c)(1),
(2), (4) Date: Feb. 21, 2006

(87) PCT Pub. No.: WO2005/026138

PCT Pub. Date: Mar. 24, 2005

(65) Prior Publication Data

US 2006/0281738 A1 Dec. 14, 2006

(30) Foreign Application Priority Data

Aug. 26, 2003 (JP) ............................. 2003-300952

(51) Int. Cl.
C07D 417/02 (2006.01)
A61K 31/541 (2006.01)

(52) U.S. Cl. .................... 514/227.2; 544/6; 544/55; 514/226.8

(58) Field of Classification Search .............. 544/6, 544/55; 514/227.2, 226.8
See application file for complete search history.

(56) References Cited

U.S. PATENT DOCUMENTS

| 5,948,777 A | 9/1999 | Bender et al. |
|---|---|---|
| 6,017,919 A | 1/2000 | Inaba et al. |
| 6,509,352 B1 | 1/2003 | Inaba et al. |
| 6,818,640 B1 | 11/2004 | Hanasaki et al. |
| 6,916,806 B2 | 7/2005 | Kai et al. |
| 2004/0082619 A1 | 4/2004 | Tada et al. |
| 2005/0009902 A1 | 1/2005 | Miyaji et al. |
| 2005/0101590 A1 | 5/2005 | Yasui et al. |

FOREIGN PATENT DOCUMENTS

| WO | 99/02499 | 1/1999 |
|---|---|---|
| WO | 01/19807 A1 | 3/2001 |
| WO | 02/072562 A1 | 9/2002 |
| WO | 03/070277 A1 | 3/2003 |
| WO | 03/035109 A1 | 5/2003 |

OTHER PUBLICATIONS

Fride, Ester, "Cannabinoids and Cystic Fibrosis: A Novel Approach to Etiology and Therapy", *Journal of Cannabis Therapeutics*, vol. 2(1), pp. 59 to 71 (2002).
Lake, K. et al., "Cardiovascular Effects of Anandamide in Anesthetized and Conscious Normotensive and Hypertensive Rats", *Hypertension*, vol. 29, No. 5, pp. 1204 to 1211 (1997).
Munro, S. et al., "Molecular characterization of a peripheral receptor for cannabinoids" *Nature*, vol. 365, pp. 61 to 65 (1993).

*Primary Examiner*—Kahsay T Habte
(74) *Attorney, Agent, or Firm*—Wenderoth, Lind & Ponack, L.L.P.

(57) ABSTRACT

The formula (I):

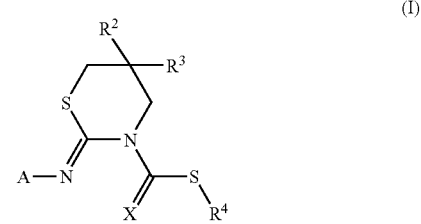

wherein each of $R^2$ and $R^3$ is, same or different, C2-C4 alkyl or the like; or $R^2$ and $R^3$ are taken together with the adjacent carbon atom to form a 5 to 8 membered non-aromatic carbocyclic ring; $R^4$ is C1-C6 alkyl or the like; X is an oxygen atom or a sulfur atom; A is the group of the formula:

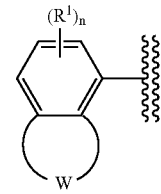

wherein $R^1$ is, same or different, alkyl or the like; W is C2-C6 alkylene which may contain an optionally substituted heteroatom(s) or the like; n is an integer of 0 to 7, a pharmaceutically acceptable salt, or a solvate thereof.

16 Claims, No Drawings

2-NAPHTHYLIMINO-1,3-THIAZINE DERIVATIVE

TECHNICAL FIELD

The present invention relates to 2-naphthylimino-1,3-thiazine derivatives having a cannabinoid receptor agonistic activity and pharmaceutical use of themselves.

BACKGROUND ART

Cannabinoid was discovered as the main active substance contained in marijuana in 1960 and found to exhibit an activity to the central nervous system (illusion, euphoria, sensory confusion of time and space) and an activity to the peripheral cell system (immunosuppressive activity, anti-inflammatory activity, analgesic activity).

After that, anandamide and 2-arachidonoylglycerol produced from phospholipid containing arachidonic acid were discovered as an endogenous cannabinoid receptor agonist. These endogenous agonists were known to exhibit an activity to the central nervous system and an activity to the peripheral cell system. It was disclosed in Non-Patent 1 that anandamide exhibits an activity to the cardiovascular system.

A cannabinoid type 1 receptor discovered in 1990 was found to distribute in the central nervous system such as the brain. Agonists to this receptor were found to suppress the release of neurotransmitters to cause central actions such as illusion or the like. A cannabinoid type 2 receptor discovered in 1993 was found to distribute in immune tissues such as the spleen or the like. Agonists to this receptor were found to suppress an activation of cells in immunocyte or phlogocyte to exhibit an immunosuppressive activity, an anti-inflammatory activity and an analgesic activity (Non-Patent 2).

It was disclosed in Non-Patent 3 that $\Delta^9$-tetrahydrocannabinol and the like exhibit bronchodilatation. Furthermore, It was disclosed in Patent 1 that a cannabinoid receptor agonism exhibits an anti-pruritus activity.

Known as compounds having a cannabinoid receptor agonistic activity are isoindolynone derivatives (Patent 2), pyrazole derivatives (Patent 3), quinolone derivatives (Patent 4 and Patent 5), pyridone derivatives (Patent 6), thiazine derivatives (Patent 7 and Patent 8), and the like.

Patent 1: WO03/035109
Patent 2: WO97/29079
Patent 3: WO98/41519
Patent 4: WO099/02499
Patent 5: WO00/40562
Patent 6: WO02/053543
Patent 7: WO01/19807
Patent 8: WO02/072562
Non-Patent 1: Hypertension (1997) 29, 1204-1210
Non-Patent 2: Nature, 1993, 365, 61-65
Non-Patent 3: Journal of Cannabis Therapeutics 2002, 2(1), 59071

DISCLOSURE OF INVENTION

The present invention provides a cannabinoid receptor agonistic activity and a pharmaceutical composition, an analgesics, a treating agent for algesic, an antipruritics or a bronchodilator containig themselves as an active ingredient.

The inventors of the present invention have found that the following 2-naphthylimino-1,3-thiazine derivatives have a strong cannabinoid receptor agonistic activity and a pharmaceutical composition contaning themselves as an active ingredient is useful for an analgesics, a treating agent for algesic, an antipruritics or a bronchodilator.

The present invention relates to 1) a compound represented by the formula (I):

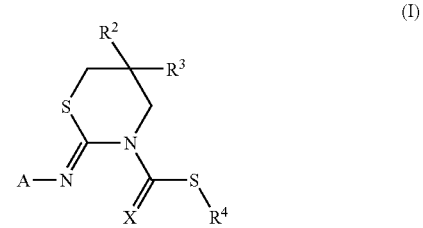

wherein each of $R^2$ and $R^3$ is, the same or different, and each is C2-C4 alkyl, C2-C4 alkenyl, C1-C4 alkoxyC1-C4 alkyl, optionally substituted aminoC1-C4 alkyl, or C3-C6 cycloalkylC1-C4 alkyl; or $R^2$ and $R^3$ are taken together with the adjacent carbon atom to form an optionally substituted 5 to 8 membered non-aromatic carbocyclic ring or an optionally substituted 5 to 8 membered non-aromatic heterocyclic ring;

$R^4$ is C1-C6 alkyl, hydroxyC1-C6alkyl, optionally substituted aminoC1-C6alkyl, or C1-C6 alkoxyC1-C6 alkyl;

X is an oxygen atom or a sulfur atom;

A is the group of the formula:

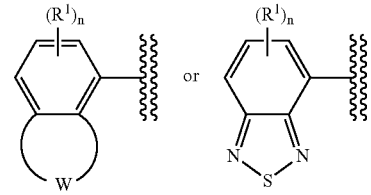

wherein $R^1$ is, same or different, alkyl, alkoxy, alkylthio, optionally substituted amino, optionally substituted aryl, optionally substituted aryloxy, optionally substituted aralkyloxy, cycloalkyl, a halogen atom, hydroxy, nitro, haloalkyl, haloalkoxy, optionally substituted carbamoyl, carboxy, alkoxycarbonyl, alkylsulfinyl, alkylsulfonyl, alkoxylalkyl, alkylthioalkyl optionally substituted aminoalkyl, alkoxyiminoalkyl, alkoxyalkoxy, alkylthioalkoxy, alkoxycarbonylalkoxy, carboxyalkoxy, alkylsulfonyloxy, optionally substituted heteroaryl, an optionally substituted non-aromatic heterocyclic group, cyano, cyanoalkoxy, or a group of the formula: —C(=O)—$R^H$ wherein $R^H$ is a hydrogen atom, alkyl, optionally substituted aryl, or an optionally substituted non-aromatic heterocyclic group;

W is C2-C6 alkylene which may contain optionally substituted a heteroatom(s) or C2-C4 alkenylene which may contain optionally substituted a heteroatom(s);

n is an integer of 0 to 7;

a pharmaceutically acceptable salt, or a solvate thereof, 2) the compound according to 1) wherein $R^2$ and $R^3$ are taken together with the adjacent carbon atom to form an optionally substituted 5 to 6 membered carbocyclic ring, a pharmaceutically acceptable salt, or a solvate thereof, 3) the compound according to 1) or 2) wherein W is —CH₂CH₂CH₂—, —CH₂CH₂CH₂CH₂—, —OCH₂O—, —OCH₂CH₂O—, —N(CH₃)CH₂CH₂CH₂—, or —CH=CH—CH=CH—, a pharmaceutically acceptable salt, or a solvate thereof,
4) a compound of the formula (II):

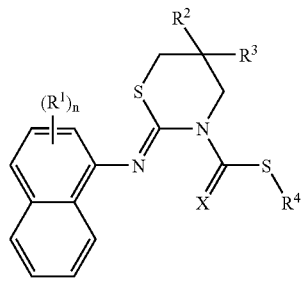

(II)

wherein R¹ is, same or different, alkyl, alkoxy, optionally substituted amino, a halogen atom, hydroxy, haloalkyl, haloalkoxy, cyano, or alkoxycarbonylalkoxy;
each of R² and R³ is, same or different, C2-C4 alkyl; or
R² and R³ are taken together with the adjacent carbon atom to form 5 to 6 membered cycloalkane;
R⁴ is C1-C6 alkyl;
X is an oxygen atom or a sulfur atom;
n is an integer of 0 to 7;
a pharmaceutically acceptable salt, or a solvate thereof,
5) the compound according to 4) wherein R¹ is a fluorine atom, a chlorine atom, dimethylamino, cyano, or t-butoxycarbonylmethoxy, a pharmaceutically acceptable salt, or a solvate thereof,
6) the compound according to 4) or 5) wherein n is 0 or 1, a pharmaceutically acceptable salt, or a solvate thereof,
7) a compound of the formula (III):

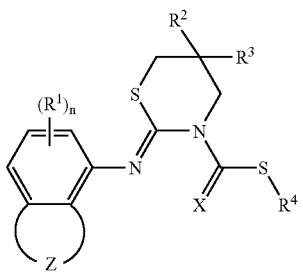

(III)

wherein R¹ is, same or different, alkyl, alkoxy, optionally substituted amino, a halogen atom, hydroxy, haloalkyl, haloalkoxy, cyano, or alkoxycarbonylalkoxy;
each of R² and R³ is, same or different, C2-C4 alkyl; or
R² and R³ are taken together with the adjacent carbon atom to form 5 to 6 membered cycloalkane;
R⁴ is C1-C6 alkyl;
X is an oxygen atom or a sulfur atom;
Z is —CH₂CH₂CH₂—, —CH₂CH₂CH₂CH₂—, or —OCH₂CH₂O—;
n is an integer of 0 to 3;
a pharmaceutically acceptable salt, or a solvate thereof,
8) the compound according to 7) wherein Z is —CH₂CH₂CH₂— or —CH₂CH₂CH₂CH₂—, a pharmaceutically acceptable salt, or a solvate thereof,
9) the compound according to 7) wherein Z is —OCH₂CH₂O—, a pharmaceutically acceptable salt, or a solvate thereof,
10) the compound according to any one of 7) to 9) wherein n is 0, a pharmaceutically acceptable salt, or a solvate thereof,
11) the compound according to any one of 4) to 10) wherein R² and R³ are taken together with the adjacent carbon atom to form 6 membered cycloalkane, a pharmaceutically acceptable salt, or a solvate thereof,
12) the compound according to any one of 1) to 11) wherein each of R² and R³ is, same or different, C2-C3 alkyl, a pharmaceutically acceptable salt, or a solvate thereof,
13) the compound according to any one of 1) to 11) wherein R⁴ is methyl or ethyl, a pharmaceutically acceptable salt, or a solvate thereof,
14) a pharmaceutical composition which contains the compound according to any one of 1) to 13), a pharmaceutically acceptable salt, or a solvate thereof as an active ingredient,
15) a pharmaceutical composition which contains the compound according to any one of 1) to 13), which has a cannabinoid receptor agonistic activity, a pharmaceutically acceptable salt, or a solvate thereof as an active ingredient,
16) the pharmaceutical composition according to any one of 14) or 15) which is useful for an analgesics,
17) the pharmaceutical composition according to any one of 14) or 15) which is useful as a treating agent for algesic,
18) the pharmaceutical composition according to any one of 14) or 15) which is useful for an antipruritics,
19) the pharmaceutical composition according to any one of 14) or 15) which is useful for a bronchodilator,
20) a method for treating a disease related to a cannabinoid receptor which comprises administering the compound according to any one of 1) to 13), a pharmaceutically acceptable salt, or a solvate thereof,
21) use of the compound according to any one of 1) to 13) for manufacturing a treating agent for a disease related to a cannabinoid receptor, a pharmaceutically acceptable salt, or a solvate thereof.

The meaning of each term are shown as follows. Each term is used to express the same meaning employed alone or in combination with other terms in the specification.

The term "halogen atom" means a fluorine atom, a chlorine atom, a bromine atom, and an iodine atom.

The term "heteroatom" includes a nitrogen atom, an oxygen atom, and a sulfur atom.

The term "alkyl" includes straight- or branched chain C1-C10 alkyl. Examples are methyl, ethyl, n-propyl, isopropyl, n-butyl, isobutyl, sec-butyl, t-butyl, n-pentyl, isopentyl, neo-pentyl, n-hexyl, n-heptyl, n-octyl, n-nonyl, n-decyl, and the like. Especially, preferable is straight- or branched chain C1-C4 alkyl. For example, preferable are methyl, ethyl, n-propyl, isopropyl, n-butyl, isobutyl, sec-butyl, and t-buty. When number of carbon atom is designated, means "alkyl" having designated number of carbon atom.

The term "cycloalkylalkyl" includes the above-mentioned "alkyl" substituted with one or more the below-mentioned "cycloalkyl". Examples are cyclopropylmethyl, 2-cyclopentylethyl, 2-cyclohexylethyl, 2-cyclohexylpropyl, and the like.

The term "hydroxyalkyl" includes the above-mentioned, "alkyl" substituted with one or more hydroxy. Examples are 2-hydroxyethyl, 3-hydroxypropyl, and the like.

The term "alkoxyalkyl" includes the above-mentioned "alkyl" substituted with one or more the below-mentioned "alkoxy". Examples are methoxymethyl, 2-methoxyethyl, 2-ethoxyethyl, 3-methoxypropyl, and the like.

The term "alkylthioalkyl" includes the above-mentioned "alkyl" substituted with one or more the below-mentioned "alkylthio". Examples are methylthiomethyl, 2-methylthioethyl, 2-ethylthioethyl, 3-methylthiopropyl, and the like.

The term "optionally substituted aminoalkyl" includes the above-mentioned "alkyl" substituted with one or more the below-mentioned "optionally substituted amino". Examples are methylamiomethyl, 2-dimethylamioethyl, 2-diethylamioethyl, 3-dimethylamiopropyl, and the like.

The term "alkoxyiminoalkyl" includes the above-mentioned "alkyl" substituted with one or more the below-mentioned imino group substituted with the below-mentioned "alkoxy". Examples are methoxyimiomethyl, 2-methoxyimioethyl, 2-ethoxyimioethyl, 2-methoxyimiopropyl, and the like.

The term "alkenyl" includes straight- or branched chain C2-C8 alkenyl which is the above-mentioned "alkyl" having one or more double bond(s). Examples are vinyl, 1-propenyl, allyl, isopropenyl, 1-buteneyl, 2-buteneyl, 3-buteneyl, 3-pentenyl, 1,3-butadienyl, 3-methyl-2-butenyl, and the like. Especially, preferable is straight- or branched chain C2-C4 alkenyl. For example, preferable are allyl, isopropenyl, and 3-buteneyl. When number of carbon atom is designated, means "alkenyl" having designated number of carbon atom.

The term "alkynyl" includes straight- or branched chain C2-C8 alkynyl which is the above-mentioned "alkyl" having one or more triple bond(s). Examples are ethynyl, propargyl, and the like. Especially, preferable is straight- or branched chain C2-C4 alkynyl. For example, preferable is propargyl.

The term "haloalkyl" means the above-mentioned "alkyl" having one or more halogen atom(s). Examples are chloromethyl, dichloromethyl, difluoromethyl, trifluoromethyl, chloroethyl (e.g. 2-chloroethyl), dichloroethyl (e.g., 1,2-dichloroethyl, 2,2-chloroethyl), chloropropyl (e.g., 2-chloropropyl, 3-chloropropyl), and the like. Preferable is haloC1-C3 alkyl.

The term "C2-C6 alkylene which may contain an optionally substituted heteroatom(s)" includes straight- or branched chain C2-C6 alkylene which may contain one to three heteroatom(s) optionally substituted with alkyl. The above-mentioned "alkyl", the below-mentioned "aralkyl", the below-mentioned "aryl", the below-mentioned "heteroaryl", the below-mentioned "acyl", and the below-mentioned "alkoxycarbonyl" are exemplified as the substituent of a heteroatom(s). Examples are —CH$_2$CH$_2$CH$_2$—, —CH$_2$CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$O—, —OCH$_2$CH$_2$—, —CH$_2$CH$_2$S—, —SCH$_2$CH$_2$—, —CH$_2$CH$_2$OCH$_2$—, —OCH$_2$CH$_2$O—, —OCH$_2$O—, —N(CH$_3$)CH$_2$CH$_2$CH$_2$—, and the like. Preferable are —CH$_2$CH$_2$CH$_2$—, —CH$_2$CH$_2$CH$_2$CH$_2$—, —OCH$_2$CH$_2$O—, —OCH$_2$O—, and —N(CH$_3$)CH$_2$CH$_2$CH$_2$—.

The term "C2-C4 alkenylene which may contain an optionally substituted heteroatom(s)" includes straight- or branched chain C2-C4 alkenylene which may contain one to two heteroatom(s) optionally substituted with alkyl. The above-mentioned "alkyl", the below-mentioned "aralkyl", the below-mentioned "aryl", the below-mentioned "heteroaryl", the below-mentioned "acyl", or the below-mentioned "alkoxycarbonyl" are exemplified as the substituent of a heteroatom(s). Examples are —CH=CH—CH=CH—, —CH=CH—O—, —O—CH=CH—, —CH=CH—S—, —S—CH=CH—, —CH=CH—NH—, —NH—CH=CH—, —CH=CH—CH=N—, —N=CH—CH=CH—, and the like. Preferable are —CH=CH—CH=CH—, —CH=CH—CH=N—, and —N=CH—CH=CH—.

The term "cycloalkane" includes C3-C10 cycloalkane. Examples are cyclopropane, cyclobutane, cyclopentane, cyclohexane, cycloheptane, cyclooctane, and the like. Preferable is C5-C8 cycloalkane. Examples are cyclopentane, cyclohexane, cycloheptane, and cyclooctane. When number of carbon atom is designated, means "cycloalkane" having designated number of carbon atom.

The term "a carbocyclic ring" includes a 3 to 10 membered carbocyclic ring which may have one or more a double bond(s) and/or a triple bond(s). Example are cyclopropane, cyclobutane, cyclopentane, cyclopentene, cyclohexane, cyclohexene, cycloheptane, cycloheptene, cyclooctene, or the like. Preferable is C5-C8 cycloalkane, and examples are cyclopentane, cyclohexane, cycloheptane; cycloheptane. When number of carbon atom is designated, means "a carbocyclic ring" having designated number of carbon atom.

The term "a non-aromatic carbocyclic ring" includes a 3 to 10 membered non-aromatic carbocyclic ring which may have one or more a double bond(s) and/or a triple bond(s). Example are cyclopropane, cyclobutane, cyclopentane, cyclopentene, cyclohexane, cyclohexene, cycloheptane, cycloheptene, cyclooctene, or the like. Preferable is C5-C8 cycloalkane, and examples are exemplified cyclopentane, cyclohexane, cycloheptane, and cyclooctane. When number of carbon atom is designated, means "a non-aromatic carbocyclic ring" having designated number of carbon atom.

The term "cycloalkyl" includes C3-C10 cycloalkyl. Examples are cyclopropyl, cyclobutyl, cyclopentyl, cyclohexyl, cycloheptyl, cyclooctyl, or the like. Preferable is C3-C6 cycloalkyl, and examples are cyclopropyl, cyclobutyl, cyclopentyl, and cyclohexyl. When number of carbon atom is designated, means "cycloalkyl" having designated number of carbon atom.

The term "aryl" includes a C6-C14 aryl, and examples are phenyl, naphthyl, anthryl, phenanthryl, or the like. Especially, preferable are phenyl and naphthyl.

The term "aralkyl" includes the above-mentioned "alkyl" substituted with the above-mentioned "aryl". Examples are benzyl, phenylethyl (e.g., 1-phenylethyl, 2-phenylethyl), phenylpropyl (e.g., 1-phenylpropyl, 2-phenylpropyl, 3-phenylpropyl), naphthylmethyl (e.g., 1-naphthylmethyl, 2-naphthylmethyl), or the like. Especially, preferable are benzyl and naphthylmethyl.

The term "heteroaryl" includes C1-C9 heteroaryl having one to four nitrogen atom(s), oxygen atom(s) and/or sulfur atom(s). Examples are furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo [b]furyl), benzothienyl (e.g., 2-benzo[b]thienyl, 3-benzo [b]thienyl, 4-benzo [b]thienyl, 5-benzo [b]thienyl, 6-benzo[b]thienyl, 7-benzo [b]thienyl), benzimidazolyl (e.g., 1-benzimidazolyl, 2-benzimidazolyl, 4-benzimidazolyl, 5-benzimidazolyl), dibenzofuryl, benzoxazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiadinyl (e.g., 1-phenothiadinyl, 2-phenothiadinyl, 3-phenothiadinyl, 4-phenothiadinyl), and the like.

The term "a non-aromatic heterocyclic group" includes a C1-C9 non-aromatic heterocyclic group having one to four nitrogen atom(s), oxygen atom(s) and/or sulfur atom(s). Examples are 1-pyrrolinyl, 2-pyrrolinyl, 3-pyrrolinyl, pyrrolidino, 2-pyrrolidinyl, 3-pyrrolidinyl, piperidino, 2-piperidyl, 3-piperidyl, 4-piperidyl, piperazino, 2-piperazinyl, 2-morpholinyl, 3-morpholinyl, morpholino, tetrahydropyranyl, or the like. Especially, preferable are morpholino, pyrrolidino, piperidino, and piperazino.

The term "non-aromatic heterocyclic ring" includes a C1-C9 non-aromatic ring having one to four nitrogen atom(s), oxygen atom(s) and/or sulfur atom(s). Examples are tetrahydrofuran, tetrahydrothiophen, pyrrolidine, tetrahydropyran, piperidine, morpholine, and the like. Especially, preferable are tetrahydrothiophen and piperidine.

The alkyl part of "alkoxy" is defined as the above "alkyl". Methoxy, ethoxy, n-propoxy, isopropoxy, n-butoxy, isobutoxy, sec-butoxy, t-butoxy, n-pentyloxy, n-hexyloxy, n-heptyloxy, n-octyloxy, and the like are exemplified as "alkoxy". Preferable is C1-C4 alkoxy, and examples are methoxy, ethoxy, n-propoxy, isopropoxy, n-butoxy, i-butoxy, sec-butoxy or t-butoxy. When number of carbon atom is designated, means "alkoxy" having designated number of carbon atom.

The term "haloalkoxy" means the above "alkoxy" substituted with one or more halogen. Examples are dichloromethoxy, difluoromethoxy, trifluoromethoxy, trifluoroethoxy (2,2,2-trifluoroethoxy), and the like. Especially, preferable are difluoromethoxy, and trifluoromethoxy.

The term "aryloxy" includes an oxygen atom substituted with the above "aryl". Examples are phenoxy, naphthoxy (e.g., 1-naphthoxy, 2-naphthoxy), anthryloxy (e.g., 1-anthryloxy, 2-anthryloxy), phenanthryl (e.g., 1-phenanthryl, 2-phenanthryl), and the like. Especially, preferable are phenoxy and naphthoxy.

The term "aralkyloxy" includes an oxygen atom substituted with the above "aralkyl". Examples are benzyloxy, phenethyloxy, and the like. Especially, preferable is benzyloxy.

The term "alkoxyalkoxy" includes the above-mentioned "alkoxy" substituted with the above-mentioned "alkoxy". Examples are methoxymethoxy, ethoxymethoxy, n-propoxymethoxy, isopropoxymethoxy, 1-methoxyethoxy, 2-methoxyethoxy, and the like. Especially, preferable are 1-methoxyethoxy and 2-methoxyethoxy.

The term "alkylthioalkoxy" includes the above-mentioned "alkoxy" substituted with the below-mentioned "alkylthio". Examples are methylthiomethoxy, ethylthiomethoxy, n-propylthiomethoxy, isopropylthiomethoxy, 1-methylthioethoxy, 2-methylthioethoxy, and the like. Especially, preferable are 1-methylthioethoxy and 2-methylthioethoxy.

The term "carboxyalkoxy" includes the above-mentioned "alkoxy" substituted with one or more "carboxy". Examples are carboxymethoxy, 2-carboxyethoxy, and the like.

The term "alkoxycarbonylalkoxy" means the above-mentioned "alkoxy" substituted with the below-mentioned "alkoxycarbonyl". Examples are methoxycarbonylmethoxy, ethoxycarbonylmethoxy, n-propoxycarbonylmethoxy, i-propoxycarbonylmethoxy, n-butoxycarbonylmethoxy, i-butoxycarbonylmethoxy, sec-butoxycarbonylmethoxy, tert-butoxycarbonylmethoxy, 2-(tert-butoxycarbonyl)ethoxy, 2-(n-pentyloxycarbonyl)ethoxy, 2-(n-hexyloxycarbonyl)ethoxy, n-heptyloxycarbonylmethoxy, n-octyloxycarbonylmethoxy, and the like. Especially, preferable are tert-butoxycarbonylmethoxy and 2-(tert-butoxycarbonyl)ethoxy.

The term "cyanoalkoxy" includes the above-mentioned "alkoxy" substituted with one or more "cyano". Examples are cyanomethoxy, 2-cyanoethoxy, and the like.

The alkyl part of "alkylthio" is defined as above-mentioned "alkyl". Examples are methylthio, ethylthio, n-propylthio, isopropylthio, n-butylthio, isobutylthio, sec-butylthio, t-butylthio, n-pentylthio, n-hexylthio and the like. Especially, preferable is C1-C4 straight- or branched chain alkylthio, and examples are methylthio, ethylthio, n-propylthio, i-propylthio, n-butylthio, i-butylthio, sec-butylthio, and t-butylthio.

Non-substituted amino, C1-C4 alkylamino, (C1-C4 alkyl) carbonylamino, aryl carbonylamino, N-(C1-C4 alkyl)carbonyl-C1-C4 alkylamino, aralkylamino, C1-C4 alkylsulfonylamino, C2-C4 alkenyloxycarbonylamino, (C1-C4 alkoxy) carbonylamino, C2-C4 alkenylamino, arylcarbonylamino, and heteroarylcarbonylamino are exemplified as "optionally substituted amino". Especially, preferable are non-substituted amino, C1-C4 alkylamino, (C1-C4 alkyl)carbonylamino, and (C1-C4 alkoxy)carbonylamino.

Methylamino, ethylamino, n-propylamino, i-propylamino, dimethylamino, diethylamino, ethylmethylamino, and propylmethylamino are exemplified as C1-C4 alkylamino. Acetylamino, formylamino, and propionylamino are exemplified as (C1-C4 alkyl)carbonylamino. Benzoylamino is exemplified as arylcarbonylamino. N-acetylmethylamino is exemplified as N—(C1-C4 alkyl)carbonyl-C1-C4 alkylamino. Benzylamino, 1-phenylethylamino, 2-phenylethylamino, 1-phenylpropylamino, 2-phenylpropylamino, 3-phenylpropylamino, 1-naphthylmethylamino, 2-naphthylmethylamino, and dibenzylamino are exemplified as aralkylamino. Methanesulfonylamino and ethanesulfonylamino are exemplified as C1-C4 alkylsulfonylamino. Vinyloxycarbonylamino and allyloxycarbonylamino are exemplified as alkenyloxycarbonylamino. Methoxycaronylamino, ethoxycaronylamino, and t-butoxycaronylamino are exemplified as (C1-C4 alkoxy)carbonylamino. Vinylamino or allylamino are exemplified as C2-C4 alkenylamono. Benzoylamino is exemplified as arylcarbonylamino. Pyridinecarboylamino is exemplified as heteroarylcarbonylamino.

The term "acyl" means carbonyl substituted with the group except for a hydrogen atom. Examples are alkylcarbonyl (e.g., acetyl, propionyl, butyryl, isobutyryl, valeryl, isovaleryl, pivaloryl, hexanoyl, octanoyl, lauroyl), alkenylcarbonyl (e.g., acryloyl, methacryloyl), cycloalkylcarbonyl (e.g., cyclopropanecarbonyl, cyclobutanecarbonyl, cyclopentanecarbonyl, cyclohexanecarbonyl), arylcarbonyl (e.g., benzoyl, naphthoyl), and heteroarylcarbonyl (e.g., pyridinecarbonyl). These groups may be substuituted with alkyl, a halogen atom, and the like. Toluoyl which is an example of arylcarbonyl substituted with alkyl and trifluoroacetyl which is an example of alkylcarbonyl substituted with a halogen atom(s) are exemplified.

The term "alkoxycarbonyl" means carbonyl substituted with the above-mentioned "alkoxy". Examples are methoxycarbonyl, ethoxycarbonyl, n-propoxycarbonyl, i-propoxycarbonyl, n-butoxycarbonyl, i-butoxycarbonyl, sec-butoxycarbonyl, tert-butoxycarbonyl, n-pentyloxycarbonyl, n-hexyloxycarbonyl, n-heptyloxycarbonyl, n-hexyloxycarbonyl, n-heptyloxycarbonyl, n-octyloxycarbonyl, and the like. Preferable are methoxycarbonyl, ethoxycarbonyl and the like.

Alkyl (e.g., methyl, ethyl, n-propyl, i-propyl), acyl (e.g., formyl, acetyl, propionyl, benzoyl) and the like are exemplified as the substituents of "optionally substituted carbamoyl". The nitrogen atom of a carbamoyl group may be mono- or di-substituted with these substituents. Preferable are carbmoyl, N-methyl carbmoyl, N-ethyl carbmoyl, and the like as "optionally substituted carbamoyl".

The alkyl part of "alkylsulfinyl" is defined as the above-mentioned "alkyl". Methanesulfinyl, ethanesulfinyl and the like are exemplified as "alkylsulfinyl".

The alkyl part of "alkylsulfonyl" is defined as the above-mentioned "alkyl". Methanesulfonyl, ethanesulfonyl and the like are exemplified as "alkylsulfonyl".

The alkylsulfonyl part of "alkylsulfonyloxy" is defined as the above-mentioned "alkylsulfonyl". Methanesulfonyloxy, ethanesulfonyloxy, and the like are exemplified as "alkylsulfonyloxy".

When "optionally substituted aryl", "optionally substituted heteroaryl", "an optionally substituted non-aromatic carbocyclic ring", "an optionally substituted non-aromatic heterocyclic ring", "an optionally substituted non-aromatic heterocyclic group ", "optionally substituted aryloxy", or "optionally substituted aralkyloxy" has substituent(s), these groups are substituted at any position(s) with one to four of substituents which may be same or different.

Hydroxy, carboxy, a halogen atom (a fluorine atom, a chlorine atom, a bromine atom, an iodine atom), haloalkyl (e.g., $CF_3$, $CH_2CF_3$, $CH_2CCl_3$), haloalkoxy, alkyl (e.g., methyl, ethyl, isopropyl, tert-butyl), alkenyl (e.g., vinyl), formyl, acyl (e.g., acetyl, propionyl, butyryl, pivoloyl, benzoyl, pyridinecarbonyl, cyclopentanecarbonyl, cyclohexanecarbonyl), alkynyl (e.g., ethynyl), cycloalkyl (e.g., cyclopropyl, cyclobutyl, cyclopentyl, cyclohexyl), alkoxy (e.g., methoxy, ethoxy, propoxy, butoxy), alkoxycarbonyl (e.g., methoxycarbonyl, ethoxycarbonyl, tert-butoxycarbonyl), nitro, nitroso, oxo, optionally substituted amino (e.g., amino, alkylamino (e.g., methylamino, ethylamino, dimethylamino), formylamino, acylamino (e.g., acetylamino, benzoylamino), aralkylamino (e.g., benzylamino, tritylamino)), azido, aryl (e.g., phenyl), aryloxy (e.g., phenoxy), cyano, isocyano, isocyanato, thiocyanato, isothiocyanato, mercapto, alkylthio (e.g., methylthio, ethylthio), alkylsulfonyl (e.g., methanesulfonyl, ethanesulfonyl), arylsuslfonyl (e.g., benzensulfonyl), optionally substituted carbamoyl, sulfamoyl, formyloxy, haloformyl, oxalo, thioformyl, thiocarboxy, dithiocarboxy, thiocarbamoyl, sulfino, sulfo, sulfoamino, hydrazino, ureido, amidino, guanidino, formyloxy, thioxo, alkoxyalkoxy, alkylthioalkoxy, and the like are exemplified as their substituents.

The following groups are exemplified as "$R^2$ and $R^3$ are taken together with the adjacent carbon atom to form an optionally substituted 5 to 8 membered non-aromatic carbocyclic ring".

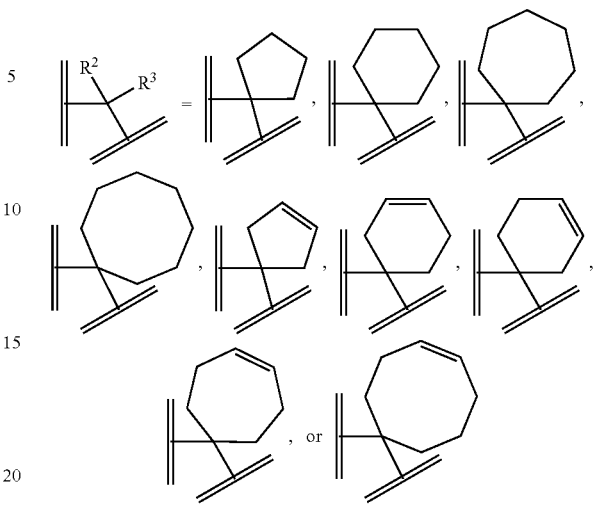

Especially, preferable is 5 or 6 membered cycloalkane formed by $R^2$ and $R^3$ taken together with the adjacent carbon atom.

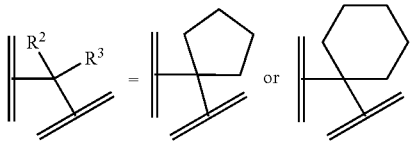

Substsituents groups (Ia) to (Ip) are shown as preferable substitsuent(s) groups for $(R^1)_n$, $R^2$ to $R^4$, X, and W of the compound represented by the formula (I).

$(R^1)_n$: (Ia) a hydrogen atom, a halogen atom, alkyl, haloalkyl, hydroxy, alkoxy, haloalkoxy, optionally substituted amino, cyano, or alkoxycarbonyl, (Ib) a hydrogen atom, a halogen atom, alkyl, alkoxy, optionally substituted amino, cyano, or alkoxycarbonyl, (Ic) a hydrogen atom, a halogen atom, optionally substituted amino, cyano, or alkoxycarbonyl.

$R^2$: (Id) C2-C4 alkyl or C2-C4 alkenyl, (Ie) C2-C4 alkyl.

$R^3$: (If) C2-C4 alkyl or C2-C4 alkenyl, (Ig) C2-C4 alkyl.

$R^4$: (Ih) C1-C8 alkyl or C1-C6 alkoxy, (Ie) C1-C8 alkyl.

X: (Ii) an oxygen atom or a sulfur atom.

W: (Ik) C2-C6 alkylene may contain an optionally substituted heteroatom(s) or C2-C4 alkenylene may contain an optionally substituted heteroatom(s), (Il) C3-C6 alkylene or C3-C4 alkenylene may contain a heteroatom(s), (Im) C3-C6 alkylene, (In) C3-C4 alkenylene may contain a heteroatom(s)

$R^2$ and $R^3$ are taken together with the adjacent carbon atom to form (Io) a 5 to 8 membered carbocyclic ring, (Ip) 5 to 6 membered cyaloalkane.

Examples of preferable group ot the compound represented by the formula (I) contains [$(R^1)_n$, $R^2$, $R^3$, $R^4$, X, W]=[Ia, Id, If, Ih, Ij, Ik], [Ia, Id, If, Ih, Ij, Il], [Ia, Id, If, Ih, Ij, Im], [Ia, Id, If, Ih, Ij, In], [Ia, Id, If, Ii, Ij, Ik], [Ia, Id, If, Ii, Ij, Il], [Ia, Id, If, Ii, Ij, Im], [Ia, Id, If, Ii, Ij, In], [Ia, Id, Ig, Ih, Ij, Ik], [Ia, Id, Ig, Ih, Ij, Il], [Ia, Id, Ig, Ih, Ij, Im], [Ia, Id, Ig, Ih, Ij, In], [Ia, Id, Ig, Ii, Ij, Ik], [Ia, Id, Ig, Ii, Ij, Il], [Ia, Id, Ig, Ii, Ij, Im], [Ia, Id, Ig, Ii, Ij, In], [Ia, Ie, If, Ih, Ij, Ik], [Ia, Ie, If, Ih, Ij, Il], [Ia, Ie, If, Ih, Ij, Im], [Ia, Ie, If, Ih, Ij, In], [Ia, Ie, If, Ii, Ij, Ik], [Ia, Ie, If, Ii, Ij, Il], [Ia, Ie, If, Ii, Ij, Im], [Ia, Ie, If, Ii, Ij, In],

[Ia, Ie, Ig, Ih, Ij, Ik], [Ia, Ie, Ig, Ih, Ii, Il], [Ia, Ie, Ig, Ih, Ij, Im], [Ia, Ie, Ig, Ih, Ij, In], [Ia, Ie, Ig, Ii, Ij, Ik], [Ia, Ie, Ig, Ii, Ij, Im], [Ia, Ie, Ig, Ii, Ij, Im], [Ia, Ie, Ig, Ii, Ij, In], [Ib, Id, If, Ih, Ij, Ik], [Ib, Id, If, Ih, Ii, Il], [Ib, Id, If, Ih, Ij, Im], [Ib, Id, If, Ih, Ij, In], [Ib, Id, If, Ii, Ij, Ik], [Ib, Id, If, Ii, Ij, Il], [Ib, Id, If, Ii, Ij, Im], [Ib, Id, If, Ii, Ij, In], [Ib, Id, Ig, Ih, Ij, Ik], [Ib, Id, Ig, Ih, Ij, Il], [Ib, Id, Ig, Ih, Ij, Im], [Ib, Id, Ig, Ih, Ii, In], [Ib, Id, Ig, Ii, Ij, Ik], [Ib, Id, Ig, Ii, Ij, Il], [Ib, Id, Ig, Ii, Ij, Im], [Ib, Id, Ig, Ii, Ij, In], [Ib, Ie, If, Ih, Ij, Ik], [Ib, Ie, If, Ih, Ij, Il], [Ib, Ie, If, Ih, Ij, Im], [Ib, Ie, If, Ih, Ij, In], [Ib, Ie, If, Ii, Ij, Ik], [Ib, Ie, If, Ii, Ij, Il], [Ib, Ie, If, Ii, Ij, Im], [Ib, Ie, If, Ii, Ij, In], [Ib, Ie, Ig, Ih, Ij, Ik], [Ib, Ie, Ig, Ih, Ij, Il], [Ib, Ie, Ig, Ih, Ij, Im], [Ib, Ie, Ig, Ih, Ij, In], [Ib, Ie, Ig, Ii, Ij, Ik], [Ib, Ie, Ig, Ii, Ij, Il], [Ib, Ie, Ig, Ii, Ij, Im], [Ib, Ie, Ig, Ii, Ij, In], [Ic, Id, If, Ih, Ij, Ik], [Ic, Id, If, Ih, Ij, Il], [Ic, Id, If, Ih, Ij, Im], [Ic, Id, If, Ih, Ij, In], [Ic, Id, If, Ii, Ij, Ik], [Ic, Id, If, Ii, Ij, Il], [Ic, Id, If, Ii, Ij, Im], [Ic, Id, If, Ii, Ij, In], [Ic, Id, Ig, Ih, Ij, Ik], [Ic, Id, Ig, Ih, Ii, Il], [Ic, Id, Ig, Ih, Ij, Im], [Ic, Id, Ig, Ih, Ij, In], [Ic, Id, Ig, Ii, Ij, Ik], [Ic, Id, Ig, Ii, Ij, Il], [Ic, Id, Ig, Ii, Ij, Im], [Ic, Id, Ig, Ii, Ij, In], [Ic, Ie, If, Ih, Ij, Ik], [Ic, Ie, If, Ih, Ij, Il], [Ic, Ie, If, Ih, Ij, Im], [Ic, Ie, If, Ih, Ij, In], [Ic, Ie, If, Ii, Ij, Ik], [Ic, Ie, If, Ii, Ij, Il], [Ic, Ie, If, Ii, Ij, Im], [Ic, Ie, If, Ii, Ij, In], [Ic, Ie, Ig, Ih, Ij, Ik], [Ic, Ie, Ig, Ih, Ij, Il], [Ic, Ie, Ig, Ih, Ij, Im], [Ic, Ie, Ig, Ih, Ij, In], [Ic, Ie, Ig, Ii, Ij, Ik], [Ic, Ie, Ig, Ii, Ij, Il], [Ic, Ie, Ig, Ii, Ij, Im], [Ic, Ie, Ig, Ii, Ij, In], or [$(R^1)_n$, $R^2$-$R^3$, $R^4$, X, W]=[Ia, Io, Ih, Ij, Ik], [Ia, Io, Ih, Ij, Il], [Ia, Io, Ih, Ij, Im], [Ia, Io, Ih, Ij, In], [Ia, Io, Ii, Ij, Ik], [Ia, Io, Ii, Ij, Il], [Ia, Io, Ii, Ij, Im], [Ia, Io, Ii, Ij, In], [Ia, Ip, Ih, Ij, Ik], [Ia, Ip, Ih, Ij, Il], [Ia, Ip, Ih, Ij, Im], [Ia, Ip, Ih, Ij, In], [Ia, Ip, Ii, Ij, Ik], [Ia, Ip, Ii, Ij, Il], [Ia, Ip, Ii, Ij, Im], [Ia, Ip, Ii, Ij, In], [Ib, Io, Ih, Ij, Ik], [Ib, Io, Ih, Ij, Il], [Ib, Io, Ih, Ij, Im], [Ib, Io, Ih, Ij, In], [Ib, Io, Ii, Ij, Ik], [Ib, Io, Ii, Ij, Il], [Ib, Io, Ii, Ij, Im], [Ib, Io, Ii, Ij, In], [Ib, Ip, Ih, Ij, Ik], [Ib, Ip, Ih, Ij, Il], [Ib, Ip, Ih, Ij, Im], [Ib, Ip, Ih, Ij, In], [Ib, Ip, Ii, Ij, Ik], [Ib, Ip, Ii, Ij, Il], [Ib, Ip, Ii, Ij, Im], [Ib, Ip, Ii, Ij, In], [Ic, Io, Ih, Ij, Ik], [Ic, Io, Ih, Ij, Il], [Ic, Io, Ih, Ij, Im], [Ic, Io, Ih, Ij, In], [Ic, Io, Ii, Ij, Ik], [Ic, Io, Ii, Ij, Il], [Ic, Io, Ii, Ij, Im], [Ic, Io, Ii, Ij, In], [Ic, Ip, Ih, Ii, Ik], [Ic, Ip, Ih, Ij, Il], [Ic, Ip, Ih, Ij, Im], [Ic, Ip, Ih, Ij, In], [Ic, Ip, Ii, Ij, Ik], [Ic, Ip, Ii, Ij, Il], [Ic, Ip, Ii, Ij, Im], [Ic, Ip, Ii, Ij, In].

Substsituents groups (IIa) to (IIk) are shown as preferable substitsuent(s) groups for $(R^1)_n$, $R^2$ to $R^4$, and X of the compound represented by the formula (II).

$(R^1)_n$: (IIa) a hydrogen atom, a halogen atom, alkyl, alkoxy, optionally substituted amino, cyano, or alkoxycarbonyl, (IIb) a hydrogen atom, a halogen atom, optionally substituted amino, cyano, or alkoxycarbonyl.

$R^2$: (IIc) C2-C4 alkyl.
$R^3$: (IId) C2-C4 alkyl.
$R^4$: (IIe) C1-C6 alkyl, (IIf) C1-C2 alkyl.

X: (IIg) an oxygen atom or a sulfur atom, (IIh) an oxygen atom, (IIi) a sulfur atom.

Or, $R^2$ and $R^3$ are taken together with the adjacent carbon atom to form (IIj) a 5 to 6 membered carbocyclic ring, (IIk) 6 membered cyaloalkane.

Examples of preferable group ot the compound represented by the formula (II) contains [$(R^1)n$, $R^2$, $R^3$, $R^4$, X]= [IIa, IIc, IId, IIe IIg], [IIa, IIc, IId, IIe IIh], [IIa, IIc, IId, IIe IIi], [IIa, IIc, IId, IIf IIg], [IIa, IIc, IId, IIf IIh], [IIa, IIc, IId, IIf IIi], [IIb, IIc, IId, IIe IIg], [IIb, IIc, IId, IIe IIh], [IIb, IIc, IId, IIe IIi], [IIb, IIc, IId, IIf IIg], [IIb, IIc, IId, IIf IIh], [IIb, IIc, IId, IIf IIi], or [$(R^1)_n$, $R^2$-$R^3$, $R^4$, X]=[IIa, IIj, IIe, IIg], [IIa, IIj, IIe, IIh], [IIa, IIj, IIe, IIi], [IIa, IIj, IIf, IIg], [IIa, IIj, IIf, IIh], [IIa, IIj, IIf, IIi], [IIa, IIk, IIe, IIg], [IIa, IIk, IIe, IIh], [IIa, IIk, IIe, IIi], [IIa, IIk, IIf, IIg], [IIa, IIk, IIf, IIh], [IIa, IIk, IIf, IIi], [IIb, IIj, IIe, IIg], [IIb, IIj, IIe, IIh], [IIb, IIj, IIe, IIi], [IIb, IIj, IIf, IIg], [IIb, IIj, IIf, IIh], [IIb, IIj, IIf, IIi], [IIb, IIk, IIe, IIg], [IIb, IIk, IIe, IIh], [IIb, IIk, IIe, IIi], [IIb, IIk, IIf, IIg], [IIb, IIk, IIf, IIh], [IIb, IIk, IIf, IIi].

Substsituents groups (IIIa) to (IIIn) are shown as preferable substitsuent(s) groups for $(R^1)_n$, $R^2$ to $R^4$, and X of the compound represented by the formula (III).

$(R^1)_n$: (IIIa) a hydrogen atom, a halogen atom, alkyl, alkoxy, optionally substituted amino, cyano, or alkoxycarbonyl, (IIIb) a hydrogen atom, a halogen atom, optionally substituted amino, cyano, or alkoxycarbonyl.

$R^2$: (IIIc) C2-C4 alkyl.
$R^3$: (IIId) C2-C4 alkyl.
$R^4$: (IIIe) C1-C6 alkyl, (IIIf) C1-C2 alkyl.

X: (IIIg) an oxygen atom or a sulfur atom, (IIIh) an oxygen atom, (IIIi) a sulfur atom.

$R^2$ and $R^3$ are taken together with the adjacent carbon atom to form (IIIj) a 5 to 6 membered cyaloalkane, (IIIk) 6 membered cyaloalkane.

Or, Z: (IIIl) —CH$_2$CH$_2$CH$_2$— or —CH$_2$CH$_2$CH$_2$CH$_2$—, (IIIm) —CH$_2$CH$_2$CH$_2$CH$_2$—, (IIIn) —OCH$_2$O—.

Examples of preferable group ot the compound represented by the formula (III) contains [$(R^1)_n$, $R^2$, $R_3$, $R^4$, X, Z]=[IIIa, IIIc, IIId, IIIe IIIg, IIIl], [IIIa, IIIc, IIId, IIIe, IIIg, IIIm], [IIIa, IIIc, IIId, IIIe, IIIg, IIIn], [IIIa, IIIc, IIId, IIIe, IIIh, IIIl], [IIIa, IIIc, IIId, IIIe, IIIh, IIIm], [IIIa, IIIc, IIId, IIIe, IIIh, IIIn], [IIIa, IIIc, IIId, IIIe, IIIi, IIIl], [IIIa, IIIc, IIId, IIIe, IIIi, IIIm], [IIIa, IIIc, IIId, IIIe, IIIi, IIIn], [IIIa, IIIc, IIId, IIIf, IIIg, IIIl], [IIIa, IIIc, IIId, IIIf, IIIg, IIIm], [IIIa, IIIc, IIId, IIIf, IIIg, IIIn], [IIIa, IIIc, IIId, IIIf, IIIh, IIIl], [IIIa, IIIc, IIId, IIIf, IIIh, IIIm], [IIIa, IIIc, IIId, IIIf, IIIh, IIIn], [IIIa, IIIc, IIId, IIIf, IIIi, IIIl], [IIIa, IIIc, IIId, IIIf, IIIi, IIIm], [IIIa, IIIc, IIId, IIIf, IIIi, IIIn], [IIIb, IIIc, IIId, IIIe, IIIg, IIIl], [IIIb, IIIc, IIId, IIIe, IIIg, IIIm], [IIIb, IIIc, IIId, IIIe, IIIg, IIIn], [IIIb, IIIc, IIId, IIIe, IIIh, IIIl], [IIIb, IIIc, IIId, IIIe, IIIh, IIIm], [IIIb, IIIc, IIId, IIIe, IIIh, IIIn], [IIIb, IIIc, IIId, IIIe, IIIi, IIIl], [IIIb, IIIc, IIId, IIIe, IIIi, IIIm], [IIIb, IIIc, IIId, IIIe, IIIi, IIIn], [IIIb, IIIc, IIId, IIIf, IIIg, IIIl], [IIIb, IIIc, IIId, IIIf, IIIg, IIIm], [IIIb, IIIc, IIId, IIIf, IIIg, IIIn], [IIIb, IIIc, IIId, IIIf, IIIh, IIIl], [IIIb, IIIc, IIId, IIIf, IIIh, IIIm], [IIIb, IIIc, IIId, IIIf, IIIh, IIIn], [IIIb, IIIc, IIId, IIIf, IIIi, IIIl], [IIIb, IIIc, IIId, IIIf, IIIi, IIIm], [IIIb, IIIc, IIId, IIIf, IIIi, IIIn], or [$(R^1)_n$, $R^2$-$R^3$, $R^4$, X, Z]=[IIIa, IIIj, IIIe, IIIg, IIIl], [IIIa, IIIj, IIIe, IIIg, IIIm], [IIIa, IIIj, IIIe, IIIg, IIIn], [IIIa, IIIj, IIIe, IIIh, IIIl], [IIIa, IIIj, IIIe, IIIh, IIIm], [IIIa, IIIj, IIIe, IIIh, IIIn], [IIIa, IIIj, IIIe, IIIi, IIIl], [IIIa, IIIj, IIIi, IIIm], [IIIa, IIIj, IIIe, IIIi, IIIn], [IIIa, IIIj, IIIf, IIIg, IIIm], [IIIa, IIIj, IIIf, IIIg, IIIn], [IIIa, IIIj, IIIf, IIIh, IIIl], [IIIa, IIIj, IIIf, IIIh, IIIm], [IIIa, IIIj, IIIf, IIIh, IIIn], [IIIa, IIIj, IIIf, IIIi, IIIl], [IIIa, IIIj, IIIf, IIIi, IIIm], [IIIa, IIIj, IIIf, IIIi, IIIn], [IIIa, IIIk, IIIe, IIIg, IIIl], [IIIa, IIIk, IIIe, IIIg, IIIm], [IIIa, IIIk, IIIe, IIIg, IIIn], [IIIa, IIIk, IIIe, IIIh, IIIl], [IIIa, IIIk, IIIe, IIIh, IIIm], [IIIa, IIIk, IIIe, IIIh, IIIn], [IIIa, IIIk, IIIe, IIIi, IIIl], [IIIa, IIIk, IIIe, IIIi, IIIm], [IIIa, IIIk, IIIe, IIIi, IIIn], [IIIa, IIIk, IIIf, IIIg, IIIl], [IIIa, IIIk, IIIf, IIIg, IIIm], [IIIa, IIIk, IIIf, IIIg, IIIn], [IIIa, IIIk, IIIf, IIIh, IIIl], [IIIa, IIIk, IIIf, IIIh, IIIm], [IIIa, IIIk, IIIf, IIIh, IIIn], [IIIa, IIIk, IIIf, IIIi, IIIl], [IIIa, IIIk, IIIf, IIIi, IIIm], [IIIa, IIIk, IIIf, IIIi, IIIn], [IIIb, IIIj, IIIe, IIIg, IIIl], [IIIb, IIIj, IIIe, IIIg, IIIm], [IIIb, IIIj, IIIe, IIIg, IIIn], [IIIb, IIIj, IIIe, IIIh, IIIl], [IIIb, IIIj, IIIe, IIIh, IIIm], [IIIb, IIIj, IIIe, IIIh, IIIn], [IIIb, IIIj, IIIe, IIIi, IIIl], [IIIb, IIIj, IIIe, IIIi, IIIm], [IIIb, IIIj, IIIe, IIIi, IIIn], [IIIb, IIIj, IIIf, IIIg, IIIl], [IIIb, IIIj, IIIf, IIIg, IIIm], [IIIb, IIIj, IIIf, IIIg, IIIn], [IIIb, IIIj, IIIf, IIIh, IIIl], [IIIb, IIIj, IIIf, IIIh, IIIm], [IIIb, IIIj, IIIf, IIIh, IIIn], [IIIb, IIIj, IIIf, IIIi, IIIl], [IIIb, IIIj, IIIf, IIIi, IIIm], [IIIb, IIIj, IIIf, IIIi, IIIn], [IIIb, IIIk, IIIe, IIIg, IIIl], [IIIb, IIIk, IIIe, IIIg, IIIm], [IIIb, IIIk, IIIe, IIIg, IIIn], [IIIb, IIIk, IIIe, IIIh, IIIl], [IIIb, IIIk, IIIe, IIIh, IIIm], [IIIb, IIIk, IIIe, IIIh, IIIn], [IIIb, IIIk, IIIe, IIIi, IIIl], [IIIb, IIIk, IIIe, IIIi, IIIm], [IIIb, IIIk, IIIe, IIIi, IIIn], [IIIb, IIIk, IIIf, IIIg, IIIl], [IIIb, IIIk, IIIf, IIIg, IIIm], [IIIb, IIIk, IIIf, IIIg, IIIn], [IIIb, IIIk, IIIf, IIIh, IIIl], [IIIb, IIIk, IIIf, IIIh, IIIm], [IIIb, IIIk, IIIf, IIIh, IIIn], [IIIb, IIIk, IIIf, IIIi, IIIl], [IIIb, IIIk, IIIf, IIIi, IIIm], [IIIb, IIIk, IIIf, IIIi, IIIn].

BEST MODE FOR CARRYING OUT THE INVENTION

The compounds of the present Invention can be synthesized by the following routes

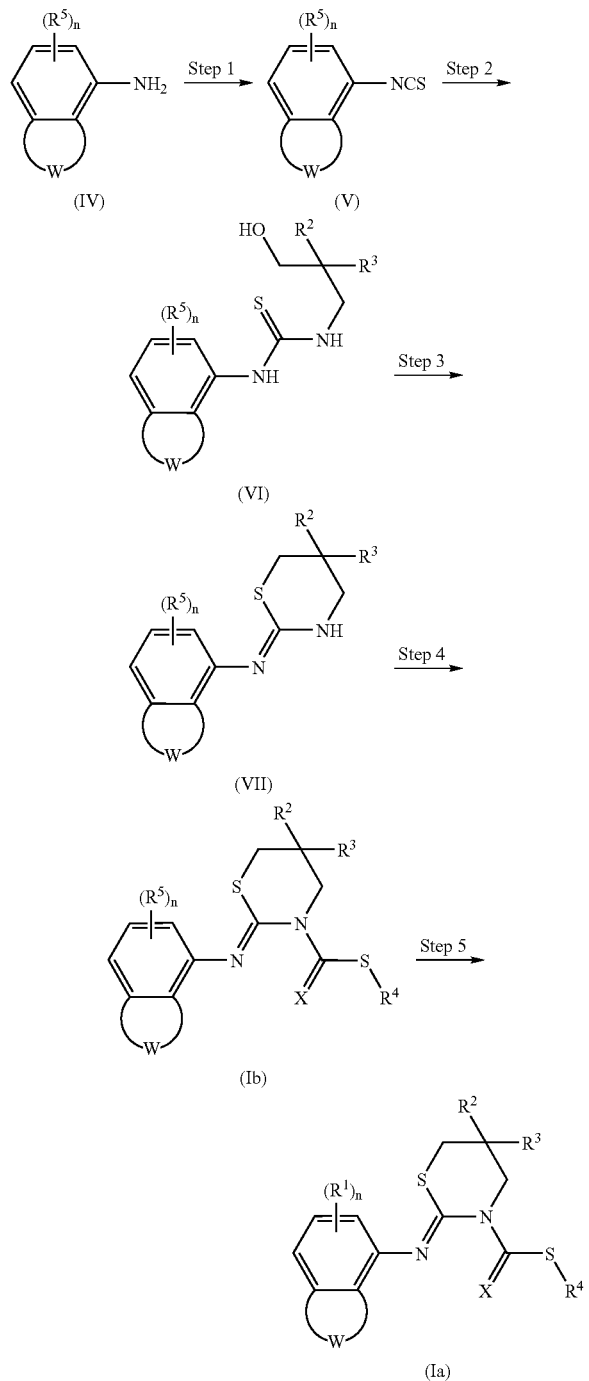

wherein $R^1$ is, the same or different, alkyl, alkoxy, alkylthio, optionally substituted amino, optionally substituted aryl, optionally substituted aryloxy, optionally substituted aralkyloxy, cycloalkyl, a halogen atom, hydroxy, nitro, haloalkyl, haloalkoxy, optionally substituted carbamoyl, carboxy, alkoxycarbonyl, alkylsulfinyl, alkylsulfonyl, alkoxylalkyl, alkylthioalkyl, optionally substituted aminoalkyl, alkoxyiminoalkyl, alkoxyalkoxy, alkylthioalkoxy, alkoxycarbonylalkoxy, carboxyalkoxy, alkylsulfonyloxy, optionally substituted heteroaryl, an optionally substituted non-aromatic heterocyclic group, cyano, cyanoalkoxy, or a group of the formula: —C(=O)—$R^H$ wherein $R^H$ is a hydrogen atom, alkyl, optionally substituted aryl, or an optionally substituted non-aromatic heterocyclic group;

$R^2$ and $R^3$ are the same or different and each is C2-C4 alkyl, C2-C4 alkenyl, C1-C4 alkoxyC1-C4 alkyl, optionally substituted aminoC1-C4 alkyl, or C3-C6 cycloalkylC1-C4 alkyl; or $R^2$ and $R^3$ are taken together with the adjacent carbon atom may form an optionally substituted 5 to 8 membered non-aromatic carbocyclic ring or an optionally substituted 5 to 8 membered non-aromatic heterocyclic ring;

$R^4$ is C1-C6 alkyl, hydroxyalkyl may be protected by the protecting group, optionally substituted aminoalkyl, or C1-C6 alkoxyC1-C6 alkyl;

$R^5$ is, same or different, alkyl, alkoxy, alkylthio, optionally substituted amino, optionally substituted amino may be protected by the protecting group, optionally substituted aryl, optionally substituted aryloxy, optionally substituted aralkyloxy, cycloalkyl, a halogen atom, hydroxy protected by the protecting group, nitro, haloalkyl, haloalkoxy, optionally substituted carbamoyl, carboxy protected by the protecting group, alkoxycarbonyl, alkylsulfinyl, alkylsulfonyl, alkoxylalkyl, alkylthioalkyl, optionally substituted aminoalkyl, alkoxyiminoalkyl, alkoxyalkoxy, alkylthioalkoxy, alkoxycarbonylalkoxy, carboxyalkoxy, alkylsulfonyloxy, optionally substituted heteroaryl, an optionally substituted non-aromatic heterocyclic group, cyano, cyanoalkoxy, or a group of the formula: —C(=O)—$R^H$ wherein $R^H$ is a hydrogen atom, alkyl, optionally substituted aryl, or an optionally substituted non-aromatic heterocyclic group;

X is an oxygen atom or a sulfur atom;

A is the group of the formula:

W is C2-C6 alkylene which contain a optionally substituted heteroatom(s) or C2-C4 alkenylene which contain an optionally substituted heteroatom(s);

n is an integer of 0 to 7.

Step 1

This is a process for producing a compound of the formula (V) which comprises converting an amino group of a compound of the formula (IV) to isothiocyanic acid ester (isothiocyanate).

A method for converting an amino group to isothio cyanic acid ester (isothiocyanate) includes the following methods; (1) a method which comprises reacting the starting compound with carbon disulfide in the presence of a base such as ammonia ($NH_3$, $NH_4OH$), triethylamine ($Et_3N$) and reacting the obtained dithiocarbamate with ethyl chlorocarboxylate ($ClCO_2Et$) and triethylamine ($Et_3N$), (2) a method which comprises reacting the above dithiocarbamate with acid metalate such as lead nitrate or the like, (3) a method of reacting thiophosgene ($CSCl_2$) and (4) a method of reacting thiocarbonyldlimidazole or the like.

In the above (1), a base (1.0 to 1.5 mole equivalent) and carbon disulfide (1.0 to 1.5 mole equivalent) are added to a solution of a compound of the formula (III) in an aprotic solvent (e.g., diethylether, tetrahydrofuran, dimethylformamide, benzene, toluene, dichloromethane, chloroform) and the mixture is stirred for 0.5 to 10 hours. After that, ethyl chlorocarboxylate (1.0 to 1.5 mole equivalent) and triethylamine (1.0 to 1.5 mole equivalent) are added thereto and the mixture is stirred in the same solvent for 0.5 to 10 hours. The reaction temperature is preferably 0 to 100° C., especially 0° C. to room temperature.

In the above (3), thiophosgene (1.0 to 1.5 mole equivalent) is added to a solution of the compound of the formula (IV) in an aprotic solvent (e.g., diethylether, tetrahydrofuran, dimethylformamide, benzene, toluene, dichloromethane, chloroform) and stirred for 0.5 to 10 hours. The reaction temperature is preferably 0 to 100° C., especially 0° C. to room temperature.

In the above (4), thiocarbonyldiimidazole (1.0 to 1.5 mole equivalent) is added to a solution of the compound of the formula (IV) in an aprotic solvent (e.g., diethylether, tetrahydrofuran, dimethylformamide, benzene, toluene, dichloromethane, chloroform) and stirred for 0.5 to 10 hours. The reaction temperature is preferably 0 to 100° C., especially 0° C. to room temperature.

1-Aminonaphthalene, 1-amino-2-fluoronaphthalene,1-amino-3-fluoronaphthalene, 1-amino-4-fluoronaphthalene, 1-amino-5-fluoronaphthalene, 1-amino-6-fluoronaphthalene, 1-amino-7-fluoronaphthalene, 1-amino-8-fluoronaphthalene, 1-amino-2-chloronaphthalene, 1-amino-3-chloronaphthalene, 1-amino-4-chloronaphthalene, 1-amino-5-chloronaphthalene, 1-amino-6-chloronaphthalene, 1-amino-7-chloronaphthalene, 1-amino-8-chloronaphthalene, 1-amino-2-bromonaphthalene, 1-amino 3-bromonaphthalene, 1-amino-4-bromonaphthalene, 1-amino-5-bromonaphthalene, 1-amino-6-bromonaphthalene, 1-amino-7-bromonaphthalene, 1-amino-8-bromonaphthalene, 1-amino-2-methylnaphthalene, 1-amino-3-methylnaphthalene, 1-amino-4-methylnaphthalene, 1-amino-5-methylnaphthalene, 1-amino-6-methylnaphthalene, 1-amino-7-methylnaphthalene, 1-amino-8-methylnaphthalene, 1-amino-2-methoxynaphthalene, 1-amino-3-methoxynaphthalene, 1-amino-4-methoxynaphthalene, 1-amino-5-methoxynaphthalene, 1-amino-6-methoxynaphthalene, 1-amino-7-methoxynaphthalene, 1-amino-8-methoxynaphthalene,1-amino-2-N,N-dimethylaminonaphthalene, 1-amino-3-N,N-dimethylaminonaphthalene, 1-amino-4-N,N-dimethylaminonaphthalene, 1-amino-5-N,N-dimethylaminonaphthalene, 1-amino-6-N,N-dimethylaminonaphthalene, 1-amino-7-N,N-dimethylaminonaphthalene, 1-amino-8-N,N-dimethylaminonaphthalene, 1-amino-2-benzyloxynaphthalene, 1-amino-3-benzyloxynaphthalene, 1-amino-4-benzyloxynaphthalene, 1-amino-5-benzyloxynaphthalene, 1-amino-6-benzyloxynaphthalene, 1-amino-7-benzyloxynaphthalene, 1-amino-8-benzyloxynaphthalene, 1-amino4-(2-pyridyl)naphthalene, 1-amino-2-trifluoromethylnaphthalene, 1-amino-3-trifluoromethylnaphthalene, 1-amino-4-trifluoromethylnaphthalene, 1-amino-5-trifluoromethylnaphthalene, 1-amino-6-trifluoromethylnaphthalene, 1-amino-7-trifluoromethylnaphthalene, 1-amino-8-trifluoromethylnaphthalene, 1-amino-2-trifluoromethoxynaphthalene, 1-amino-3-trifluoromethoxynaphthalene, 1-amino-4-trifluoromethoxynaphthalene, 1-amino-5-trifluoromethoxynaphthalene, 1-amino-6-trifluoromethoxynaphthalene, 1-amino-7-trifluoromethoxynaphthalene, 1-amino-8-trifluoromethoxynaphthalene, 1-amino-2-cyanonaphthalene, 1-amino-3-cyanonaphthalene, 1-amino-4-cyanonaphthalene, 1-amino-5-cyanonaphthalene, 1-amino-6-cyanonaphthalene, 1-amino-7-cyanonaphthalene, 1-amino-8-cyanonaphthalene and the like are exemplified as the compound of the formula (IV).

Step 2

This is a process for producing a compound of the formula (VI) which comprises reacting an isothiocyanate of the compound of the formula (V) with $NH_2$—$CH_2C(R^2R^3)CH_2$—OH wherein $R^2$ and $R^3$ are defined as above.

This process can be carried out in an aprotic solvent (e.g., diethylether, tetrahydrofuran, dimethylformamide, benzene, toluene, dichloromethane, chloroform).

The reaction temperature is preferably 0 to 100° C., especially 0° C. to room temperature. The reaction time is 0.5 to 10 hours.

The amount of $NH_2$—$CH_2C(R^2R^3)CH_2$—OH is 1.0 to 1.5 mole equivalent to that of the compound of the formula (IV).

3-Amino-2,2-diethylpropanol, 3-amino-2,2-di(n-propyl)propanol, 3-amino-2,2-diisopropylpropanol, 3-amino-2,2-di(n-butyl)propanol, (1-aminomethyl-1-cyclopentyl)metahnol, (1-aminomethyl-1-cyclohexyl)methanol, (1-aminomethyl-1-cycloheptyl) methanol, (1-aminomethyl-1-cyclooctyl)methanol, (4-aminomethyl-4-tetrapyranyl) methanol, (4-aminomethyl-N-methyl-4-piperidinyl)methanol, and the like are exemplified as $NH_2$—$CH_2C(R^2R^3)CH_2$—OH.

Step 3

This is a process for producing a compound of the formula (VII) which comprises the cyclization of the compound of the formula (VI).

A method of the cyclization includes (1) a method which comprises reacting with carbon tetrachloride and triphenylphosphine ($Ph_3P$), and then with potassium carbonate, (2) a method which comprises reacting with hydrochloric acid.

In the above (1), the reaction can be carried out in an aprotic solvent (e.g., diethylether, tetrahydrofuran, dimethylformamide, benzene, toluene, dichloromethane, chloroform) with stirring for 0.5 to 5 hours at 0° C. to room temperature. The amount of carbon tetrachloride and triphenylphosphine ($Ph_3P$) are 1.0 to 1.5 mole equivalent to that of the compound (V).

In the above (2), the reaction can be carried out in concentrated hydrochloric acid with refluxing for 0.5 to 10 hours.

Step 4

This is a process for producing a compound of the formula (Ib) which comprises introducing —C(=X)—$SR^4$ to a compound of the formula (Ib).

This process can be carried out by reacting with a compound of the formula: Hal—C(=X)—$SR^4$ wherein $R^4$ and X are as defined above and Hal is a halogen atom in the presence of a base (e.g., triethylamine, pyridine, N,N-dimethylaminopyridine). This process can be carried out under generally known conditions of N-acylation. For example, the reaction can be carried out in an aprotic solvent (e.g., diethylether, tetrahydrofuran, dimethylformamide, benzene, toluene, dichloromethane, chloroform) with stirring at 0 to 100° C. for 0.5 to 10 hours.

Moreover, it can be prepared by reacting with carbon dioxide ($CS_2$) in the presence of a base (e.g., sodium hydride), and reacting with alkyl halide (e.g., methyl iodide, ethyl iodide) or alkoxyalkyl halide (e.g., chloromethyl methyl ether). The reaction can be carried out in an aprotic solvent (e.g., diethylether, tetrahydrofuran, dimethylformamide, benzene, toluene, dichloromethane, chloroform) with stirring at 0° C. to room temperature.

Step 5

This is a process for producing a compound of the formula (Ia) which comprises a) deprotection or b) deprotection and alkylation wherein $R^5$ has the group protected with protecting group.

Deprotection can be carried out by the method described in Protective Groups in Organic Synthesis, Theodora W Green (John Wiley & Sons) or the like.

Alkylation can be carried out by reacting with alkyl halide (e.g., methyl iodide, ethyl iodide) or (alkoxycarbonyl)alkyl halide (e.g., t-butoxycarbonylmethy brmide) in the presence of a base (e.g., sodium hydride). The reaction can be carried out in an aprotic solvent (e.g., diethylether, tetrahydrofuran, dimethylformamide, benzene, toluene, dichloromethane, chloroform) with stirring at 0° C. to room temperature.

When A is benzthiazol-4-yl in the formula (I), it can be synthesized by the following steps. Each step can be used by similar method described above each step in preparing the formula (Ib) from the formula (IV).

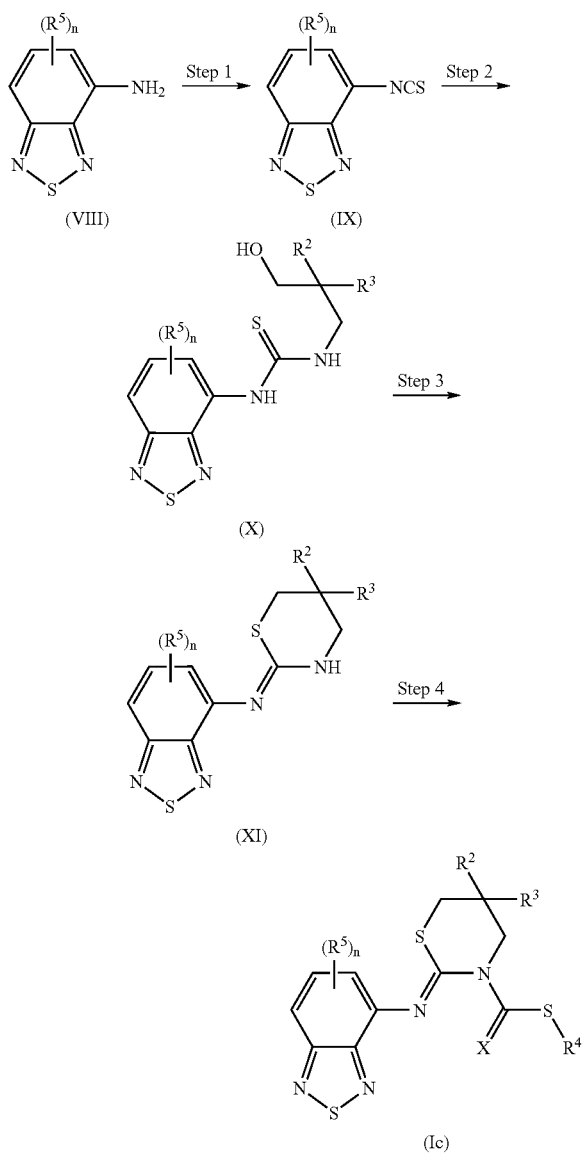

wherein $R^2$, $R^3$, $R^4$, $R^5$, and n are defined as above.

A prodrug is a derivative which is converted to a pharmaceutically active compound of the present invention under a physiological condition. Method for the selection and process of an appropriate prodrug derivative are described in the literature such as Design of Prodrugs, Elsevier, Amsterdam 1985.

A prodrug of the present invention can be prepared by introducing a leaving group to substituents on ring A which are substitutable (e.g., amino, hydroxy). Examples of a prodrug derived form a compound having an amino group includes carbamate derivatives (e.g., methylcarbamate, cyclopropylmethylcarbamate, t-butylcarbamate, benzylcarbamate), amide derivatives (e.g., formamide, acetamide), N-alkyl derivative (e.g., N-allylamine, N-methoxymethylamine) or the like. Examples of a prodrug derived form a compound having hydroxy group include ether derivatives (methoxymethylether, methoxyethoxymethylether), ester derivatives (e.g., acetate, pivaloate, benzoate) or the like.

Examples of a pharmaceutically acceptable salt include basic salts (e.g., alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts; aralkyl amine salts such as N,N-dibenzylethylenediamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts). Acid addition salts include, for example, mineral acid salts such as hydrochlorides salts, sulfates salts, nitrate salts, phosphates salts, carbonates salts, hydrogen carbonates salts or perchlorates salts; organic acid salts such as acetates, propionates, lactates, maleates, fumarates, tartrates, malates, succinates, or ascorbates; sulfonates such as methanesulfonates, isethionates, benzenesulfonates, or p-toluenesulfonates; and acidic amino acid salts such as aspartates or glutamates.

A solvate includes a solvate of the compound of the formula (I), (II), or (III) a prodrug of itself or a pharmaceutically acceptable salt thereof, for example, monosolvate, disolvate, monohydrate, dihydrate or the like.

The compound of the present invention can be used for treating or preventing diseases associated with a cannabinoid receptor agonist. For example, in nature 1993, 3(65), 61-65 it discloses that a cannabinoid receptor agonist has an anti-inflammatory activity and analgesic activity, in Journal of Cannabis Therapeutics 2000, 2(1), 59-71 it discloses that a cannabinoid receptor agonist has a bronchiectasis activity, and in WO 03/035109 it discloses that a cannabinoid receptor agonist has an antipruritics activity.

Therefore, the compound of the present invention can be used as an antiinflammatory agent, an antiallergic agent, an analgesics, an algesic agent (e.g., an algesic agent of nociceptivity, a neurogenic algesic agent, a psychogenic algesic agent, an acute algesic agent, a chronic algesic agent), an immunodeficiency disease treating agent, an immunosuppressive agent, an immunomodulating agent, an autoimmune disease treating agent, chronic rheumatoid arthritis treating agent, multiple sclerosis treating agent, an inhibitor for inflammatory cellar infiltration in the respiratory tract, an inhibitor for hyperirritability in the respiratory tract, a muciparous inhibitor, a bronchodilator an antipruritics, or the like.

When using a compound of the present invention in treatment, it can be formulated into ordinary formulations for oral and parenteral administration. A pharmaceutical composition containing a compound of the present invention can be in the form for oral and parenteral administration. Specifically, it can be formulated into formulations for oral administration such as tablets, capsules, granules, powders, syrup, and the like; those for parenteral administration such as injectable solution or suspension for intravenous, intramuscular or subcutaneous injection, inhalant, eye drops, nasal drops, suppositories, or percutaneous formulations such as ointment.

In preparing the formulations, carriers, excipients, solvents and bases known to one ordinary skilled in the art may be used. Tablets are prepared by compressing or formulating an active ingredient together with auxiliary components. Examples of usable auxiliary components include pharmaceutically acceptable excipients such as binders (e.g., cornstarch), fillers (e.g., lactose, microcrystalline cellulose), disintegrates (e.g., starch sodium glycolate) or lubricants (e.g., magnesium stearate). Tablets may be coated appropriately. In the case of liquid formulations such as syrups, solutions or suspensions, they may contain suspending agents (e.g., methyl cellulose), emulsifiers (e.g., lecithin), preservatives and the like. In the case of injectable formulations, it may be in the form of solution or suspension, or oily or aqueous emulsion, which may contain suspension-stabilizing agent or dispensing agent, and the like. In the case of an inhalant, it is formulated into a liquid formulation applicable to an inhaler. In the case of eye drops, it is formulated into a solution or a suspension.

Although an appropriate dosage of the present compound varies depending on the administration route, age, body weight, sex, or conditions of the patient, and the kind of drug(s) used together, if any, and should be determined by the physician in the end, in the case of oral administration, the daily dosage can generally be between about 0.01-100 mg, preferably about 0.01-10 mg, more preferably about 0.1-10 mg, per kg body weight. In the case of parenteral administration, the daily dosage can generally be between about 0.001-100 mg, preferably about 0.001-1 mg, more preferably about 0.01-1 mg, per kg body weight. The daily dosage can be administered in 1-4 divisions.

The following Examples are provided to further illustrate the present invention and are not to be construed as limiting the scope.

The meaning of each abbreviation are shown as follows.
Me: methyl,
Et: ethyl,
Pr: propyl,
i-Pr: isopropyl,
t-Bu: t-butyl,
Ph: phenyl,
Bn: benzyl,
DMF: N,N-dimethylformamide

EXAMPLES

Example 1

Synthesis of 3-[(methylthio)thiocarbonyl]-2-(1-naphthylimino)-5,5-pentamethylene-1,3-thiazine (I-23)

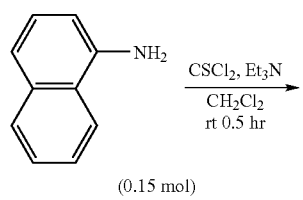

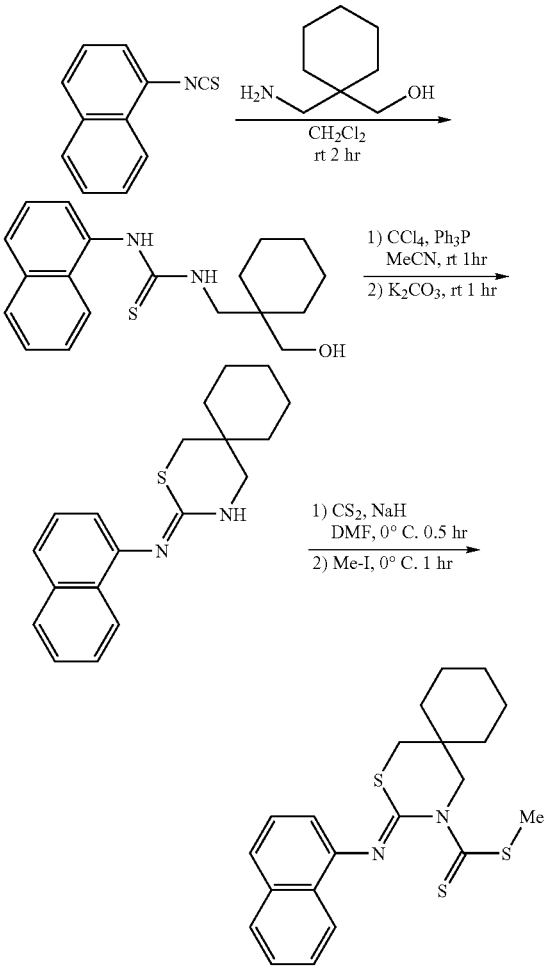

To the mixture of 1-naphthylamine (21.48 g), triethylamine (33.39 g), and dichloromethane (250 mL) was added a dicholomethane (50 mL) solution of thiophosgen (18.97 g) at bleow 20° C. over 30 minutes, and the mixture was stirred at room temperature. The reaction mixture was added into ice-water (1000 mL), extracted with diethyl ether (1000 mL). The extract was washed two times with brine (1000 mL), dried over anhydrous magnesium sulfate, evaporated under reduced pressure to obtain crude (1-naphthyl)isothiocyanate.

To a dichlorometane (100 mL) solution of the obtained crude (1-naphthyl)isothiocyanato was added a dichlorometane (50 mL) solution of 3-amino-2,2-pentamethylenepropanol (27.93 g) under ice-cooling, and the mixture was stirred at room temperature for 2 h. To the reaction mixture was added water (1000 mL), and the reaction mixture was extracted with dichlorometane (400 mL). The extract was washed with brine (500 mL), dried over anhydrous magnesium sulfate, evaporated under reduced pressure to obtain crude N-(1-naphthyl)-N'-(3-hydroxy-2,2-pentamethylenepropyl)thiourea.

To a mixture of the obtained crude N-(1-naphthyl)-N'-(3-hydroxy-2,2-pentamethylenepropyl)thiourea, triphenylphosphine (59.02 g), and acetonitrile (300 mL) was added carbon tetrachloride (69.22 g) under ice-cooling over 20 minutes. After the reaction mixtuer was stirred at room temperature for 1 h, potassium carbonate (31.10 g) was added to the reaction mixture under ice-cooling, and the reaction mixture was stirred at room temperature for 1 h. To the reaction mixture were added ic-water (400 mL) and ethyl acetate (300 mL), and the reaction mixture is crystalized. The resulting crystals were filtered to obtain 2-(1-naphthyl)-5,5-pentamethylene-1,3-thiazine (33.61 g, 72%) as colorless crystals. $^1$H-NMR (δ ppm TMS/CDCl$_3$) 1.40-1.64 (10H, m), 2.71 (2H, s), 3.17 (2H, s), 5.73 (1H, brs), 7.01 (1H, d, J=6.9), 7.35-7.47 (3H, m), 7.55 (1H, d, J=8.3), 7.81 (1H, m), 8.01 (1H, m).

To a mixture of 2-(1-naphthyl)-5,5-pentamethylene-1,3-thiazine (33.61 g), carbon disulfide (11.42 g), and DMF (200 mL) was added 60% sodium hydride (6.0 g) under ice-cooling over 5 minutes. After the reaction mixtuer was stirred at 0° C. for 30 minutes, methyl iodide (21.29 g) was added to the reaction mixture under ice-cooling over 20 minutes, and the reaction mixture was stirred at 0 for 1 h. To the reaction mixture were added ice-water (800 mL), and the reaction was extracted with diethylether (500 mL). The extract was washed with brine (1000 mL), dried over anhydrous magnesium sulfate, evaporated under reduced pressure. The obtained crude product was recrystalized from acetone/2-propanol to obtain 3-[(methylthio)thiocarbonyl]-2-(1-naphthyl)-5,5-pentamethylene-1,3-thiazine (I-23: 26.13 g, 65%) as yellow crystals.

Example 2

Synthesis of 3-[(methylthio)thiocarbonyl]-2-(7-hydroxy-1-naphthylimino)-5,5-pentamethylene-1,3-thiazine (I-62)

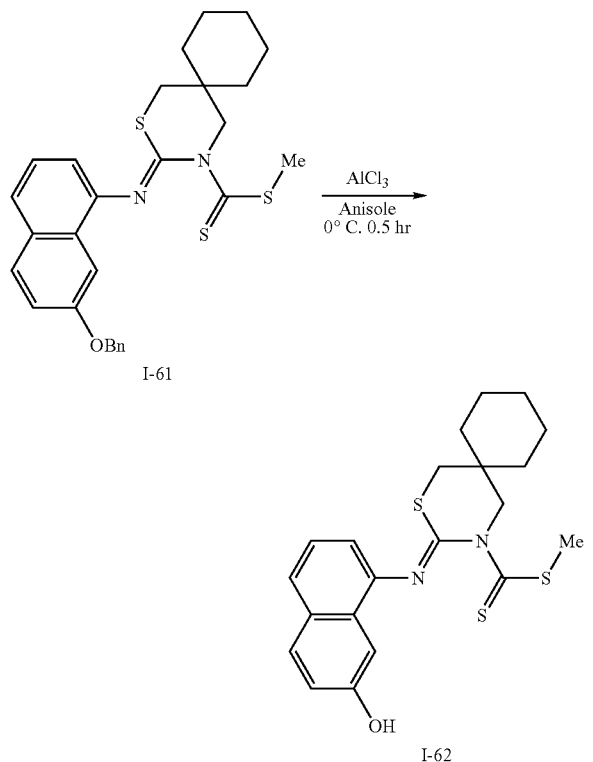

To a anisole (9 mL) of 3-[(methylthio)thiocarbonyl]-2-(7-benzyloxy-1-naphthylimino)-5,5-pentamethylene-1,3-thiazine (I-61: 0.91 g) was added aluminium chloride (0.36 g) under ice-cooling, and the reaction mixtuer was stirred at 0° C. for 30 minutes. The reaction mixture was poured into a half-saturated sodium hydrogencarbonate aqueous solution (150 mL), and the reaction was extracted with diethylether (150 mL). The extract was washed with brine (150 mL), dried over anhydrous magnesium sulfate, evaporated under reduced pressure. The obtained residue was purified by the column-chromatography on silica gel (hexane/ethyl acetate), recrystalized from diisopropyl ether/hexane to obtain 3-[(methylthio)thiocarbonyl]-2-(7-hydroxy-1-naphthyl)-5,5-pentamethylene-1,3-thiazine (I-62: 0.31 g, 41%) as yellow crystals.

Example 3

Synthesis of 3-[(methylthio)thiocarbonyl]-2-(7-t-butoxycarbonylmethoxy-1-naphthylimino)-5,5-pentamethylene-1,3-thiazine (I-89)

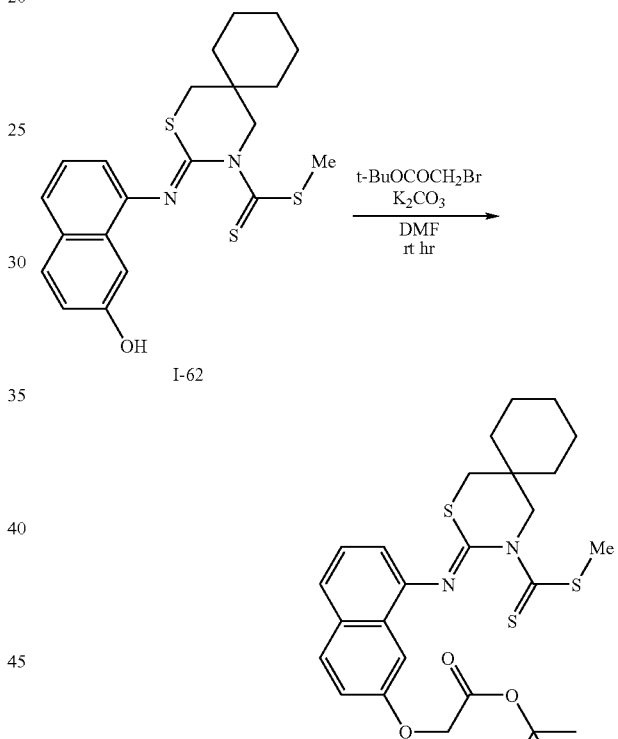

To a suspension of 3-[(methylthio)thiocarbonyl]-2-(7-hydroxy-1-naphthylimino)-5,5-pentamethylene-1,3-thiazine (I-62: 0.21 g), potassium carbonate (0.14 g), and DMF (2 mL) was added t-butyl bromoacetate (0.20 g), and the reaction mixtuer was stirred at room temperature for 1 h. The reaction mixture was poured into ice-water (80 mL), and the reaction was extracted with diethylether (100 mL). The extract was washed with brine (80 mL), dried over anhydrous magnesium sulfate, evaporated under reduced pressure. The obtained residue was purified by the column-chromatography on silica gel (hexane/ethyl acetate), recrystalized from ethyl acetate/hexane to obtain 3-[(methylthio)thiocarbonyl]-2-(7-t-butoxycarbonylmethoxy-1-naphthylimino)-5,5-pentamethylene-1,3-thiazine (1-89: 0.22 g, 83%) as yellow crystals.

Example 4

Synthesis of 3-[(methylthio)thiocarbonyl]-2-(7-carboxymethoxy-1-naphthylimino)-5,5-pentamethylene-1,3-thiazine (I-90)

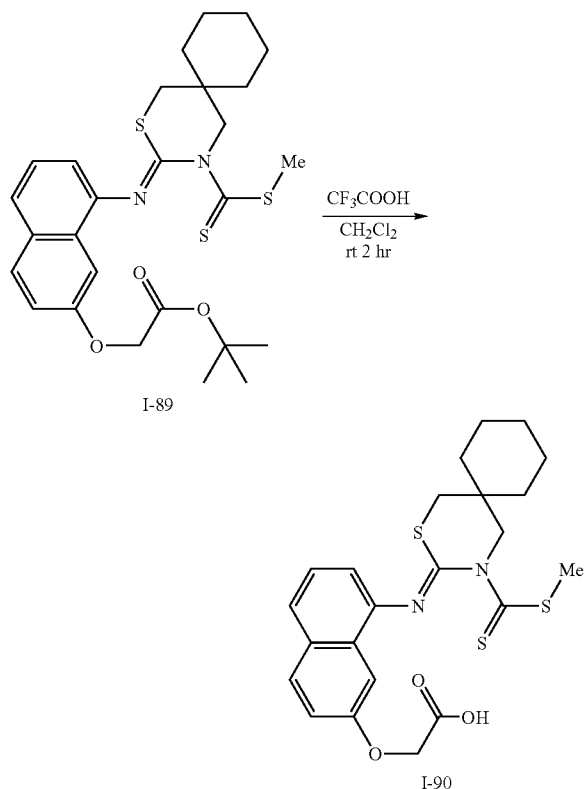

To a dichloromethane (2 mL) solution of 3-[(methylthio)thiocarbonyl]-2-(t-butoxycarbonylmethoxy-1-naphthylimino)-5,5-pentamethylene-1,3-thiazine (I-89: 0.21 g), was added trifluoroacetic acid (1 mL) under ice-cooling, and the reaction mixtuer was stirred at room temperature for 2 h. To the reaction mixture was added toluene (5 mL), and the mixture was evaporated under reduced pressure. The obtained residue was recrystalized from ethyl acetate/diisopropyl ether to obtain 3-[(methylthio)thiocarbonyl]-2-(7-carboxymethoxy-1-naphthylimino)-5,5-pentamethylene-1,3-thiazine (I-90: 0.12 g, 63%) as yellow crystals.

Example 5

Synthesis of 3-[(methylthio)thiocarbonyl]-2-(4-dimethylamino-1-naphthylimino)-5,5-diisopropyl-1,3-thiazine hydrochloric acid salt (I-152)

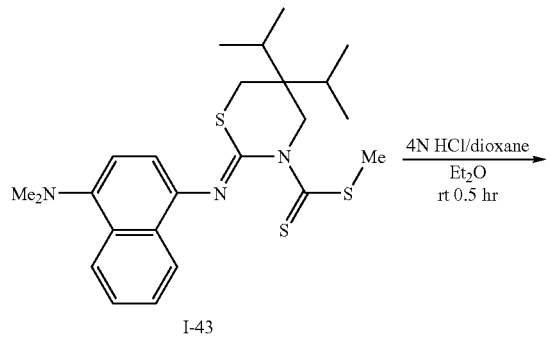

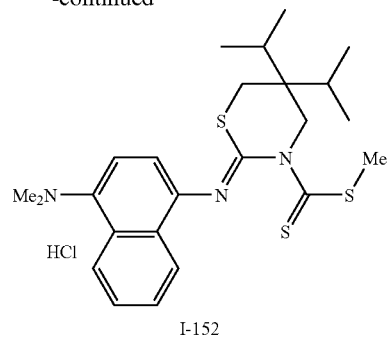

To a diethyl ether (5 mL) solution of 3-[(methylthio)thiocarbonyl]-2-(4-dimethylamino-1-naphthylimino)-5,5-diisopropyl-1,3-thiazine (I-43: 0.15 g), was added 4N dioxane solution of hydrochloric acid (0.23 mL), and the reaction mixtuer was stirred at room temperature for 0.5 h. The resulting crystals were filterd to obtain 3-[(methylthio)thiocarbonyl]-2-(4-dimethylamino-1-naphthylimino)-5,5-diisopropyl-1,3-thiazine hydrochloric acid salt (I-152: 0.14 g, 94%) as yellow crystals.

The compounds I-1 to I-22, I-24 to I-61, I-63 to I-88, and I-91 to I-151 were synthesized by the similar method described above. Structures and physical data of the Compounds I-1 to I-151 were shown in Tables 1 to 16.

TABLE 1

| No. | W | $R^2$ | $R^3$ | $R^4$ | X |
|---|---|---|---|---|---|
| I-1 | quinoline | —$(CH_2)_5$— | | Me | S |
| I-2 | quinoline | —$(CH_2)_4$— | | Me | S |
| I-3 | quinoline | Et | Et | Me | S |
| I-4 | quinoline | Pr | Pr | Me | S |
| I-5 | quinoline | Pr | Pr | Me | O |
| I-6 | tetrahydronaphthalene | —$(CH_2)_5$— | | Me | S |
| I-7 | tetrahydronaphthalene | —$(CH_2)_5$— | | Me | O |
| I-8 | tetrahydronaphthalene | Et | Et | Me | S |
| I-9 | tetrahydronaphthalene | —$(CH_2)_4$— | | Me | S |
| I-10 | tetrahydronaphthalene | i-Pr | i-Pr | Me | S |
| I-11 | tetrahydronaphthalene | Et | Et | Me | O |
| I-12 | tetrahydronaphthalene | Allyl | Allyl | Me | S |
| I-13 | tetrahydronaphthalene | —$(CH_2)_4$— | | Me | O |
| I-14 | tetrahydronaphthalene | i-Pr | i-Pr | Me | O |
| I-15 | tetrahydronaphthalene | Allyl | Allyl | Me | O |

TABLE 1-continued

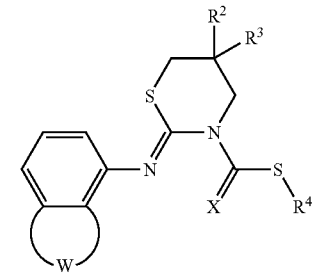

| No. | W | R² | R³ | R⁴ | X |
|---|---|---|---|---|---|
| I-16 | | Et | Et | Me | S |
| I-17 | | —(CH₂)₄— | | Me | S |
| I-18 | | —(CH₂)₅— | | Me | S |
| I-19 | | —(CH₂)₄— | | Me | O |
| I-20 | | —(CH₂)₅— | | Me | O |

TABLE 2

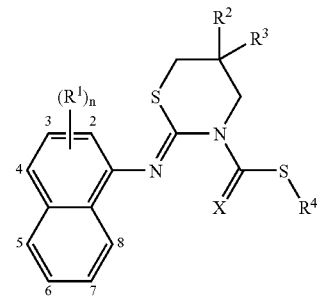

| No. | (R¹)ₙ | R² | R³ | R⁴ | X |
|---|---|---|---|---|---|
| I-21 | H | —(CH₂)₄— | | Me | S |
| I-22 | H | Pr | Pr | Me | S |
| I-23 | H | —(CH₂)₅— | | Me | S |
| I-24 | H | Et | Et | Me | S |
| I-25 | H | Pr | Pr | Me | O |
| I-26 | H | —(CH₂)₅— | | Me | O |
| I-27 | H | iPr | i-Pr | Me | S |
| I-28 | H | Allyl | Allyl | Me | S |
| I-29 | H | i-Pr | i-Pr | Me | O |
| I-30 | 2-Me | —(CH₂)₄— | | Me | S |
| I-31 | 2-Me | —(CH₂)₅— | | Me | S |
| I-32 | 4-Cl | —(CH₂)₄— | | Me | S |
| I-33 | 4-Cl | —(CH₂)₅— | | Me | S |
| I-34 | 4-Cl | —(CH₂)₄— | | Me | O |
| I-35 | 4-Cl | —(CH₂)₅— | | Me | O |
| I-36 | 2-OMe | —(CH₂)₄— | | Me | S |
| I-37 | 2-OMe | —(CH₂)₅— | | Me | S |
| I-38 | 2-OMe | i-Pr | i-Pr | Me | S |
| I-39 | 4-OMe | —(CH₂)₅— | | Me | S |
| I-40 | 4-OMe | i-Pr | i-Pr | Me | S |
| I-41 | 4-Br | —(CH₂)₅— | | Me | S |
| I-42 | 4-(2-Pyridyl) | —(CH₂)₅— | | Me | S |
| I-43 | 4-N(Me)₂ | i-Pr | i-Pr | Me | S |
| I-44 | 4-N(Me)₂ | —(CH₂)₄— | | Me | S |
| I-45 | 4-N(Me)₂ | —(CH₂)₅— | | Me | S |
| I-46 | H | —(CH₂)₂O(CH₂)₂— | | Me | S |
| I-47 | H | —(CH₂)₂O(CH₂)₂— | | Me | O |

TABLE 2-continued

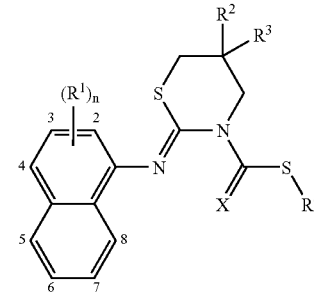

| No. | (R¹)ₙ | R² | R³ | R⁴ | X |
|---|---|---|---|---|---|
| I-48 | 7-OMe | —(CH₂)₄— | | Me | S |
| I-49 | 7-OMe | —(CH₂)₅— | | Me | S |
| I-50 | 7-OMe | i-Pr | i-Pr | Me | S |
| I-51 | H | —(CH₂)₂NMe(CH₂)₂— | | Me | S |
| I-52 | H | —(CH₂)₅— | | Et | S |
| I-53 | H | i-Pr | i-Pr | Et | S |
| I-54 | H | —(CH₂)₅— | | CH₂OMe | S |
| I-55 | H | i-Pr | i-Pr | CH₂OMe | S |
| I-56 | H | —(CH₂)₅— | | Et | O |
| I-57 | H | i-Pr | i-Pr | Et | O |
| I-58 | 6-OMe | —(CH₂)₄— | | Me | S |
| I-59 | 6-OMe | —(CH₂)₅— | | Me | S |
| I-60 | 6-OMe | i-Pr | i-Pr | Me | S |

TABLE 3

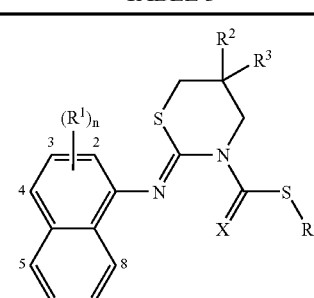

| No. | (R¹)ₙ | R² | R³ | R⁴ | X |
|---|---|---|---|---|---|
| I-61 | 7-OBn | —(CH₂)₅— | | Me | S |
| I-62 | 7-OH | —(CH₂)₅— | | Me | S |
| I-63 | 5-OMe | —(CH₂)₄— | | Me | S |
| I-64 | 5-OMe | —(CH₂)₅— | | Me | S |
| I-65 | 5-OMe | i-Pr | i-Pr | Me | S |
| I-66 | 5-OMe | —(CH₂)₄— | | Me | O |
| I-67 | 5-OMe | —(CH₂)₅— | | Me | O |
| I-68 | 5-OMe | i-Pr | i-Pr | Me | O |
| I-69 | 6-OBn | —(CH₂)₅— | | Me | S |
| I-70 | 6-OBn | i-Pr | i-Pr | Me | S |
| I-71 | 6-OH | —(CH₂)₅— | | Me | S |
| I-72 | 6-OSO₂Me | —(CH₂)₅— | | Me | S |
| I-73 | 6-OCH₂CO₂-t-Bu | —(CH₂)₅— | | Me | S |
| I-74 | 6-OCH₂CO₂H | —(CH₂)₅— | | Me | S |
| I-75 | 6-OH | i-Pr | i-Pr | Me | S |
| I-76 | 6-OSO₂Me | i-Pr | i-Pr | Me | S |
| I-77 | 6-OCH₂CO₂-t-Bu | i-Pr | i-Pr | Me | S |
| I-78 | 6-OCH₂CO₂H | i-Pr | i-Pr | Me | S |
| I-79 | 5-OBn | —(CH₂)₅— | | Me | S |
| I-80 | 5-OBn | i-Pr | i-Pr | Me | S |
| I-81 | 5-OH | —(CH₂)₅— | | Me | S |
| I-82 | 5-OH | i-Pr | i-Pr | Me | S |
| I-83 | 5-OSO₂Me | —(CH₂)₅— | | Me | S |
| I-84 | 5-OSO₂Me | i-Pr | i-Pr | Me | S |
| I-85 | 5-OCH₂CO₂-t-Bu | —(CH₂)₅— | | Me | S |
| I-86 | 5-OCH₂CO₂-t-Bu | i-Pr | i-Pr | Me | S |

TABLE 3-continued

| No. | (R¹)ₙ | R² | R³ | R⁴ | X |
|---|---|---|---|---|---|
| I-87 | 5-OCH₂CO₂H | —(CH₂)₅— | | Me | S |
| I-88 | 5-OCH₂CO₂H | i-Pr | i-Pr | Me | S |
| I-89 | 7-OCH₂CO₂-t-Bu | —(CH₂)₅— | | Me | S |
| I-90 | 7-OCH₂CO₂H | —(CH₂)₅— | | Me | S |
| I-91 | 7-OSO₂Me | —(CH₂)₅— | | Me | S |
| I-92 | 7-OCH₂CN | —(CH₂)₅— | | Me | S |
| I-93 | 7-OBn | i-Pr | i-Pr | Me | S |
| I-94 | 7-OH | i-Pr | i-Pr | Me | S |
| I-95 | 7-OCH₂CO₂-t-Bu | i-Pr | i-Pr | Me | S |
| I-96 | 7-OCH₂CO₂H | i-Pr | i-Pr | Me | S |
| I-97 | 7-OSO₂Me | i-Pr | i-Pr | Me | S |

TABLE 4

| No. | A | R² | R³ | R⁴ | X |
|---|---|---|---|---|---|
| I-98 | 4-methyl-2,1,3-benzothiadiazol-7-yl | —(CH₂)₅— | | Me | O |
| I-99 | 4-methyl-2,1,3-benzothiadiazol-7-yl | i-Pr | i-Pr | Me | O |
| I-100 | 8-methylnaphthalen-1-yl | —(CH₂)₅— | —CH₂CH₂OH | | S |
| I-101 | 8-methylnaphthalen-1-yl | —(CH₂)₅— | —CH₂CH₂OH | | S |
| I-102 | 5,6,7,8-tetrahydronaphthalen-1-yl | —(CH₂)₅— | —CH₂CH₂NMe₂ | | S |
| I-103 | 5,6,7,8-tetrahydronaphthalen-1-yl | —(CH₂)₅— | —CH₂CH₂NMe₂ | | S |
| I-104 | 7-methyl-2,3-dihydro-1H-inden-4-yl | i-Pr | i-Pr | Me | S |
| I-105 | 7-methyl-2,3-dihydro-1H-inden-4-yl | i-Pr | i-Pr | Me | O |
| I-106 | 7-methyl-2,3-dihydro-1H-inden-4-yl | n-Pr | n-Pr | Me | O |
| I-107 | 7-methyl-2,3-dihydro-1H-inden-4-yl | n-Pr | n-Pr | Me | S |
| I-108 | 5-methyl-2,3-dihydro-1,4-benzodioxin-6-yl | —(CH₂)₅— | | Me | O |
| I-109 | 5-methyl-2,3-dihydro-1,4-benzodioxin-6-yl | —(CH₂)₅— | | Me | S |

TABLE 4-continued

| No. | A | R² | R³ | R⁴ | X |
|---|---|---|---|---|---|
| I-110 | 4-methyl-1,3-benzodioxol-5-yl | —(CH₂)₅— | | Me | O |
| I-111 | 4-methyl-1,3-benzodioxol-5-yl | —(CH₂)₅— | | Me | S |
| I-112 | 1,5-dimethyl-1,2,3,4-tetrahydroquinolin-8-yl | —(CH₂)₅— | | Me | S |

TABLE 5

| No. | (R¹)ₙ | R² | R³ | R⁴ | X |
|---|---|---|---|---|---|
| I-113 | 4-Cl | i-Pr | i-Pr | Me | S |
| I-114 | 4-Cl | i-Pr | i-Pr | Me | O |
| I-115 | 4-NO₂ | —(CH₂)₅— | | Me | S |
| I-116 | 4-NO₂ | —(CH₂)₅— | | Me | O |
| I-117 | 7-OSO₂Me | —(CH₂)₅— | | Me | O |
| I-118 | 7-OCH₂CO₂-t-Bu | —(CH₂)₅— | | Me | O |
| I-119 | 7-OCH₂CO₂H | —(CH₂)₅— | | Me | O |
| I-120 | 7-OCH₂CN | —(CH₂)₅— | | Me | O |
| I-121 | 4-NO₂ | i-Pr | i-Pr | Me | S |
| I-122 | 4-NO₂ | i-Pr | i-Pr | Me | O |
| I-123 | 4-NHCOMe | i-Pr | i-Pr | Me | S |
| I-124 | 4-NH₂ | i-Pr | i-Pr | Me | S |
| I-125 | 4-NHSO₂Me | i-Pr | i-Pr | Me | S |
| I-126 | 4-N(SO₂Me)₂ | i-Pr | i-Pr | Me | S |
| I-127 | 4-NHCOPh | i-Pr | i-Pr | Me | S |
| I-128 | 4-NO₂ | n-Pr | n-Pr | Me | O |
| I-129 | 4-NO₂ | n-Pr | n-Pr | Me | S |
| I-130 | 4-NH₂ | —(CH₂)₅— | | Me | S |
| I-131 | 4-NH₂ | n-Pr | n-Pr | Me | S |
| I-132 | 4-NHCOMe | —(CH₂)₅— | | Me | S |
| I-133 | 4-OBn | —(CH₂)₅— | | Me | S |
| I-134 | 4-OBn | i-Pr | i-Pr | Me | S |
| I-135 | 4-OH | —(CH₂)₅— | | Me | S |
| I-136 | 4-OSO₂Me | —(CH₂)₅— | | Me | S |
| I-137 | 4-OEt | —(CH₂)₅— | | Me | S |
| I-138 | 4-OCH₂CN | —(CH₂)₅— | | Me | S |
| I-139 | 4-OH | i-Pr | i-Pr | Me | S |
| I-140 | 4-F | —(CH₂)₅— | | Me | S |

TABLE 5-continued

| No. | (R¹)ₙ | R² | R³ | R⁴ | X |
|---|---|---|---|---|---|
| I-141 | 4-F | —(CH₂)₅— | | Me | O |
| I-142 | 4-F | i-Pr | i-Pr | Me | S |
| I-143 | 4-F | i-Pr | i-Pr | Me | O |
| I-144 | 4-CN | —(CH₂)₅— | | Me | S |
| I-145 | 4-CN | i-Pr | i-Pr | Me | S |
| I-146 | H | —(CH₂)₅— | | —CH₂CH₂OH | S |
| I-147 | 4-F | —(CH₂)₅— | | —CH₂CH₂OH | S |
| I-148 | 4-CN | i-Pr | i-Pr | Me | O |
| I-149 | H | —(CH₂)₅— | | —CH₂CH₂CH₂OH | S |
| I-150 | H | —(CH₂)₅— | | —CH₂CH₂NMe₂ | S |
| I-151 | H | —(CH₂)₅— | | —CH₂CH₂CH₂OH | S |

TABLE 6

| Comp. No. | m.p. °C. | NMR (CDCl₃) |
|---|---|---|
| I-1 | 160–161 | 1.38-1.63(8H, m), 1.73-1.82(2H, m), 2.68(2H, s), 2.70(3H, s), 4.64(2H, s), 7.17(1H, d, J=7.3), 7.39(1H, dd, J=8.2, 4.6), 7.66-7.72(1H, m), 7.93(1H, d, J=8.2), 8.46(1H, d, J=8.2), 8.93(1H, dd, J=4.0, 1.7) |
| I-2 | 111–113 | 1.59-1.86(8H, m), 2.68(3H, m), 2.77(2H, s), 4.65(2H, s), 7.17(1H, d, J=7.6), 7.39(1H, dd, J=8.2, 4.0), 7.69(1H, m), 7.94(1H, d, J=8.6), 8.43(1H, d, J=8.6), 8.94(1H, dd, J=4.0, 2.0) |
| I-3 | 121–122 | 0.90(6H, t, J=7.3), 1.47-1.64(4H, m), 2.63(2H, s), 2.71(3H, s), 4.56(2H, s), 7.16(1H, d, J=7.6), 7.39(1H, dd, J=8.6, 4.3), 7.69(1H, dd, J=8.6, 7.6), 7.93(1H, d, J=8.6), 8.45(1H, d, J=7.6), 8.93(1H, dd, J=4.3, 1.7) |
| I-4 | 139–140 | 0.93(6H, t, J=6.9), 1.20-1.58(8H, m), 2.64(2H, s), 2.71(3H, s), 4.56(2H, s), 7.16(1H, d, J=7.6), 7.39(1H, dd, J=8.6, 4.3), 7.69(1H, dd, 8.6, 7.6), 7.93(1H, d, J=8.6), 8.46(1H, d, J=8.6), 8.93(1H, dd, J=4.3, 2.0) |
| I-5 | | 0.83-0.94(6H, m), 1.13-1.35(8H, m), 2.27(3H, s), 2.76(2H, s), 3.48(2H, s), 7.46(1H, dd, J=8.6, 4.3), 7.64(1H, dd, J=7.3, 1.0), 7.75(1H, dd, J=8.6, 7.6), 8.19(1H, m), 8.42(1H, m), 8.95(1H, dd, J=4.3, 1.0) |
| I-6 | 106–107 | 1.31-1.62(8H, m), 1.72-1.85(6H, m), 2.59(2H, s), 2.64(3H, s), 2.66(2H, s), 2.79(2H, s), 4.55(2H, s), 6.72(1H, d, J=7.9), 6.89(1H, d, J=7.9), 7.09(1H, t, J=7.6) |
| I-7 | 119.5–120.5 | 1.34-1.65(10H, m), 1.72-1.85(4H, m), 2.32(3H, s), 2.61(2H, s), 2.65(2H, s), 2.79(2H, s), 3.85(2H, s), 6.63(1H, d, J=7.6), 6.87(1H, d, J=7.6), 7.06(1H, t, J=7.6) |
| I-8 | 101.5–102.5 | 0.89(6H, t, J=7.6), 1.45-1.68(4H, m), 1.78(4H, m), 2.59(2H, m), 2.61(2H, s), 2.64(3H, s), 2.79(2H, m), 4.48(2H, s), 6.71(1H, d, J=7.6), 6.89(1H, d, J=7.6), 7.08(1H, m) |
| I-9 | 103–104 | 1.59-1.90(12H, m), 2.58(2H, m), 2.63(3H, s), 2.75(2H, s), 2.80(2H, m), 4.56(2H, s), 6.72(1H, d, J=7.6), 6.90(1H, d, J=7.6), 7.09(1H, m) |
| I-10 | 105–106 | 1.01(6H, d, J=6.9), 1.06(6H, d, J=6.9), 1.73-1.84(4H, m), 2.02(2H, sept, J=6.9), 2.59(2H, m), 2.64(3H, s), 2.78(2H, s), 2.78(2H, m), 4.66(2H, s), 6.67(1H, d, J=7.6), 6.88(1H, d, J=7.6), 7.07(1H, t, J=7.6) |
| I-11 | | 0.88(6H, t, J=7.6), 1.38-1.60(4H, m), 1.73-1.83(4H, m), 2.32(3H, s), 2.59(2H, s), 2.62(2H, m), 2.79(2H, m), 3.79(2H, s), 6.63(1H, d, J=7.3), 6.86(1H, d, J=7.3), 7.06(1H, d=7.3) |
| I-12 | | 1.76-1.81(4H, m), 2.25(2H, dd, J=13.9, 8.2), 2.39(2H, dd, J=13.9, 8.2), 2.59(2H, m), 2.65(3H, s), 2.66(2H, s), 2.80(2H, m), 4.54(2H, s), 5.15(2H, s), 5.20(2H, d, J=2.6), 5.76-5.92(2H, m), 6.72(1H, d, J=7.3), 7.09(1H, t, J=7.3) |
| I-13 | | 1.50-1.83(10H, m), 2.30(3H, s), 2.60(2H, m), 2.77(4H, m), 3.88(2H, s), 6.63(1H, d, J=7.6), 6.87(1H, d, J=7.6), 7.06(1H, t, d=7.6) |
| I-14 | 119–120 | 0.99(6H, d, J=6.9), 1.01(6H, d, J=6.9), 1.73-1.84(4H, m), 1.96(2H, sept, J=6.9), 2.31(3H, s), 2.61(2H, m), 2.72(2H, s), 2.79(2H, m), 3.98(2H, s), 6.60(1H, d, J=7.6), 6.86(1H, d, J=7.6), 7.05(1H, t, J=7.6) |
| I-15 | | 1.73-1.85(4H, m), 2.14-2.30(4H, m), 2.33(3H, s), 2.62(2H, m), 2.64(2H, s), 2.79(2H, m), 3.84(2H, s), 5.15-5.21(4H, m), 5.73-5.89(2H, m), 6.63(1H, d, J=7.6), 6.87(1H, d, J=7.6), 7.07(1H, d, J=7.6) |

TABLE 7

| Comp. No. | m.p. °C. | NMR (CDCl$_3$) |
|---|---|---|
| I-16 | 127.5-128.5 | 0.89(6H, t, J=7.3), 1.45-1.66(4H, m), 2.07(2H, quint, J=7.6), 2.61(2H, s), 2.64(3H, s), 2.88(2H, t, J=7.6), 2.95(2H, t, J=7.6), 4.48(2H, s), 6.73(1H, d, J=7.6), 7.03(1H, d, J=7.6), 7.14(1H, t, J=7.6) |
| I-17 | 110-111 | 1.65-1.88(8H, m), 2.07(2H, quint, J=7.6), 2.63(3H, s), 2.75(2H, s), 2.87(2H, t, J=7.6), 2.95(2H, t, J=7.6), 6.74(1H, d, J=7.6), 7.04(1H, d, J=7.6), 7.15(1H, m) |
| I-18 | 112-114 | 1.37-1.65(8H, m), 1.76-1.81(2H, m), 2.07(2H, quint, J=7.3), 2.64(3H, s), 2.66(2H, s), 2.88(2H, t, J=7.6), 2.95(2H, t, J=7.6), 4.56(2H, s), 6.74(1H, d, J=7.6), 7.04(1H, d, J=7.3), 7.14(1H, m) |
| I-19 | 135-136 | 1.56-1.73(8H, m), 2.06(2H, quint, J=7.3), 2.30(3H, s), 2.76(2H, s), 2.87(2H, t, J=7.6), 2.95(2H, t, J=7.6), 3.88(2H, s), 6.68(1H, d, J=7.6), 7.02(1H, d, J=7.6), 7.13(1H, m) |
| I-20 | 103-105 | 1.44-1.57(10H, m), 2.07(2H, quint, J=7.3), 2.32(3H, s), 2.65(2H, s), 2.88(2H, t, J=7.6), 2.95(2H, t, J=7.6), 3.85(2H, s), 6.69(1H, d, J=7.6), 7.02(1H, d, J=7.6), 7.13(1H, m) |
| I-21 | | 1.65-1.90(8H, m), 2.68(3H, s), 2.75(2H, s), 4.65(2H, s), 7.09(1H, d, J=7.2), 7.42-7.52(3H, m), 7.68(1H, d, J=7.2), 7.86(1H, m), 8.08(1H, d, J=7.2) |
| I-22 | 139-140.5 | 0.92(6H, t, J=7.3), 1.22-1.55(8H, m), 2.62(2H, s), 2.70(3H, s), 4.57(2H, s), 7.08(1H, d, J=7.3), 7.42-7.51(2H, m), 7.67(1H, d, J=8.2), 7.85(1H, m), 8.06(1H, m) |
| I-23 | 118-119 | 1.30-1.85(10H, m), 2.66(2H, s), 2.70(3H, s), 4.65(2H, s), 7.09(1H, d, J=7.3), 7.42-7.53(3H, m), 7.67(1H, d, J=8.2), 7.85(1H, m), 8.07(1H, m) |
| I-24 | 122.5-123.5 | 0.89(6H, t, J=7.3), 1.45-1.70(4H, m), 2.61(2H, s), 2.70(3H, s), 4.57(2H, s), 7.08(1H, dd, J=7.6, 1.0), 7.42-7.54(3H, m), 7.67(1H, d, J=8.2), 7.86(1H, m), 8.07(1H, m) |
| I-25 | 108.5-109.5 | 0.94(6H, t, J=7.3), 1.15-1.49(8H, m), 2.38(3H, s), 2.58(2H, s), 3.88(2H, s), 6.98(1H, dd, J=7.3, 1.0), 7.40-7.52(3H, m), 7.64(1H, d, J=8.2), 7.85(1H, m), 8.11(1H, m) |
| I-26 | 125.5-126.5 | 1.26-1.70(10H, m), 2.38(3H, s), 2.63(2H, s), 3.93(2H, s), 6.99(1H, dd, J=7.3, 1.3), 7.40-7.52(3H, m), 7.64(1H, d, J=8.2), 7.84(1H, dd, J=4.3, 2.3), 8.11(1H, m) |
| I-27 | 121-122 | 1.01(6H, d, J=6.9), 1.07(6H, d, J=6.9), 2.03(2H, sept, J=6.9), 2.69(3H, s), 2.77(2H, s), 4.75(2H, s), 7.04(1H, dd, J=7.6, 1.0), 7.41-7.53(3H, m), 7.65(1H, d, J=7.9), 7.84(1H, m), 8.06(1H, m) |
| I-28 | | 2.26(2H, dd, J=14.2, 8.2), 2.40(2H, dd, J=14.2, 7.3), 2.67(2H, s), 2.70(3H, s), 4.64(2H, s), 5.15(2H, m), 5.19(2H, m), 5.77-5.89(2H, m), 7.0.9(1H, d, J=7.6), 7.42-7.53(3H, m), 7.68(1H, d, J=7.9), 7.86(1H, m), 8.06(1H, m) |
| I-29 | 98-99 | 1.00(6H, d, J=6.9), 1.02(6H, d, J=6.9), 1.97(2H, sept, J=6.9), 2.37(3H, s), 2.69(2H, s), 4.07(2H, s), 6.96(1H, dd, J=7.3, 1.0), 7.38-7.52(3H, m), 7.63(1H, d, J=8.6), 7.84(1H, m), 8.11(1H, m) |
| I-30 | 118-119 | 1.55-1.94(8H, m), 2.40(3H, s), 2.69(3H, s), 2.73(2H, d, J=2.3), 4.57-4.83(2H, m), 7.34(1H, d, J=8.2), 7.40-7.45(2H, m), 7.58(1H, d, J=8.2), 7.80(1H, m), 7.97(1H, m) |
| I-31 | 134-135 | 1.31-1.84(10H, m), 2.40(3H, s), 2.64(2H, d, J=3.0), 2.71(3H, s), 4.51(1H, d, J=12.9), 4.83(1H, d, J=12.9), 7.34(1H, d, J=8.2), 7.40-7.47(2H, m), 7.58(1H, d, J=8.2), 7.40-7.47(2H, m), 7.58(1H, d, J=8.2), 7.80(1H, m), 8.00(1H, m) |

TABLE 8

| Comp. No. | m.p. °C. | NMR (CDCl$_3$) |
|---|---|---|
| I-32 | 140-141 | 1.57-1.94(8H, m), 2.68(3H, s), 2.76(2H, s), 4.64(2H, s), 7.02(1H, d, J=7.9), 7.51-7.66(3H, m), 8.06(1H, d, J=8.2), 8.27(1H, d, J=7.6) |
| I-33 | 181-182 | 1.31-1.69(8H, m), 1.73-1.86(2H, m), 2.67(2H, s), 2.70(3H, s), 4.64(2H, s), 7.02(1H, d, J=7.9), 7.51-7.66(3H, m), 8.09(1H, d, J=7.6), 8.27(1H, d, J=7.9) |
| I-34 | | 1.50-1.83(8H, m), 2.35(3H, s), 2.77(2H, s), 3.95(2H, s), 6.92(1H, d, J=7.9), 7.50-7.64(3H, m), 8.07(1H, dd, J=7.6, 1.0), 8.26(1H, dd, J=7.6, 1.3) |
| I-35 | 145.5-146.5 | 1.37-1.69(10H, m), 2.38(3H, s), 2.65(2H, s), 3.93(2H, s), 6.91(1H, d, J=7.9), 7.50-7.65(3H, m), 8.13(1H, d, J=7.6), 8.26(1H, d, J=7.6) |
| I-36 | 127-128 | 1.50-1.95(8H, m), 2.68(3H, s), 2.74(2H, s), 3.95(3H, s), 4.69(2H, s), 7.32-7.45(3H, m), 7.68(1H, d, J=8.2), 7.80(1H, d, J=7.6), 7.99(1H, d, J=8.2) |

TABLE 8-continued

| Comp. No. | m.p. °C. | NMR (CDCl₃) |
|---|---|---|
| I-37 | 137-141 | 1.32-1.85(10H, m), 2.63(2H, s), 2.70(3H, s), 3.95(3H, s), 4.68(2H, s), 7.31-7.48(3H, m), 7.68(1H, d, J=8.9), 7.80(1H, d, J=7.6), 8.02(1H, d, J=7.6) |
| I-38 | 118-119 | 1.01(6H, d, J=6.9), 1.06(6H, d, J=6.9), 2.02(2H, sept, J=6.9), 2.67(3H, s), 2.73(2H, s), 3.94(3H, s), 4.80(2H, s), 7.30-7.45(3H, m), 7.66(1H, d, J=9.2), 7.79(1H, d, J=8.2), 8.01(1H, d, J=8.2) |
| I-39 | 168-169 | 1.30-1.71(8H, m), 1.73-1.89(2H, m), 2.66(2H, s), 2.69(3H, s), 4.01(3H, s), 4.63(2H, s), 6.79(1H, d, J=8.2), 7.03(1H, d, J=7.6), 7.47-7.55(2H, m), 8.05(1H, m), 8.26(1H, m) |
| I-40 | 116-118 | 1.01(6H, d, J=6.9), 1.07(6H, d, J=6.9), 2.03(2H, sept, J=6.9), 2.69(3H, s), 2.77(2H, s), 4.01(3H, s), 4.74(2H, s), 6.79(1H, d, J=7.9), 6.98(1H, d, J=7.9), 7.47-7.53(2H, m), 8.05(1H, m), 8.26(1H, m) |
| I-41 | 187-188 | 1.30-1.69(8H, m), 1.72-1.85(2H, m), 2.67(2H, s), 2.70(3H, s), 4.64(2H, s), 6.97(1H, d, J=7.9), 7.50-7.66(2H, m), 7.75(1H, d, J=7.9), 8.08(1H, d, J=8.2), 8.24(1H, d, J=8.9) |
| I-42 | 132-133 | 1.31-1.70(8H, m), 1.75-1.90(2H, m), 2.71(5H, s), 4.68(2H, s), 7.19(1H, d, J=7.6), 7.41(1H, d, J=7.6), 7.43-7.57(3H, m), 7.80-7.89(2H, m), 8.16(1H, m), 8.68(1H, d, J=4.0), 8.78(1H, s) |
| I-43 |  | 1.01(6H, d, J=6.9), 1.07(6H, d, J=6.9), 2.05(2H, sept, J=6.9), 2.68(3H, s), 2.77(2H, s), 2.89(6H, s), 4.74(2H, s), 6.98(1H, d, J=7.9), 7.05(1H, d, J=7.9), 7.42-7.57(2H, m), 8.07(1H, m), 8.24(1H, m) |
| I-44 | 115-117 | 1.55-1.94(8H, m), 2.66(3H, s), 2.76(2H, s), 2.90(6H, s), 4.63(2H, s), 7.01-7.05(2H, m), 7.44-7.55(2H, m), 8.04(1H, m), 8.25(1H, m) |
| I-45 | 114-115.5 | 1.22-1.66(8H, m), 1.75-1.86(2H, m), 2.67(2H, s), 2.69(3H, s), 2.90(6H, s), 4.64(2H, s), 7.05(2H, m), 7.44-7.55(2H, m), 8.08(1H, m), 8.25(1H, m) |
| I-46 | 138-139 | 1.50-1.70(2H, m), 1.80-2.00(2H, m), 2.70(3H, s), 2.73(2H, s), 3.70-3.80(4H, m), 4.79(2H, s), 7.09(1H, d, J=7.3), 7.43-7.55(3H, m), 7.69(1H, d, J=8.2), 7.87(1H, m), 8.06(1H, m) |
| I-47 | 96.5-98 | 1.50-1.70(2H, m), 1.70-1.90(2H, m), 2.38(3H, s), 2.71(2H, s), 3.60-3.80(4H, m), 4.05(2H, s), 6.98(1H, dd, J=7.2, 1.0), 7.40-7.54(3H, m), 7.66(1H, d, J=8.2), 7.85(1H, m), 8.10(1H, m) |

TABLE 9

| Comp. No. | m.p. °C. | NMR (CDCl₃) |
|---|---|---|
| I-48 | 119-120 | 1.60-1.94(8H, m), 2.68(3H, s), 2.75(2H, s), 3.90(3H, s), 4.63(2H, s), 7.08(1H, dd, J=7.6, 1.3), 7.17(1H, dd, J=8.9, 2.3), 7.32(1H, m), 7.40(1H, d, J=2.4), 7.62(1H, d, J=8.2), 7.76(1H, d, J=8.9) |
| I-49 | 141-142 | 1.23-1.66(8H, m), 1.72-1.88(2H, m), 2.66(2H, s), 2.69(3H, s), 3.89(3H, s), 4.64(2H, s), 7.07(1H, d, J=7.3), 7.16(1H, dd, J=8.9, 2.6), 7.31(1H, m), 7.46(1H, d, J=2.3), 7.61(1H, d, J=8.2), 7.76(1H, d, J=8.9) |
| I-50 | 93-95 | 1.02(6H, d, J=6.9), 1.08(6H, d, J=6.9), 2.03(2H, sept, J=6.9), 2.70(3H, s), 2.77(2H, s), 3.89(3H, s), 4.74(2H, s), 7.02(1H, dd, J=7.6, 1.3), 7.16(1H, dd, J=8.9, 2.6), 7.31(1H, m), 7.44(1H, d, J=2.3), 7.59(1H, d, J=8.2), 7.75(1H, d, J=8.9) |
| I-51 | 116.5-117.5 | 1.50-1.70(2H, m), 1.90-2.10(2H, m), 2.30-2.60(4H, m), 2.32(3H, s), 2.68(2H, s), 2.70(3H, s), 4.70(2H, s), 7.09(1H, d, J=6.3), 7.42-7.55(3H, m), 7.68(1H, d, J=7.9), 7.86(1H, m), 8.06(1H, m) |
| I-52 | 119-120 | 1.30-1.70(8H, m), 1.39(3H, t, J=7.4), 1.70-1.90(2H, m), 2.65(2H, s), 3.32(2H, q, J=7.4), 4.63(2H, s), 7.10(1H, m), 7.42-7.54(3H, m), 7.67(1H, d, J=8.2), 7.85(1H, m), 8.08(1H, m) |
| I-53 | 95.5-97 | 1.01(1H, d, J=6.9), 1.06(6H, d, J=6.9), 1.37(3H, t, J=7.4), 2.02(2H, sept, J=6.9), 2.76(2H, s), 3.31(2H, q, J=7.4), 4.71(2H, s), 7.05(1H, d, J=6.6), 7.41-7.53(3H, m), 7.65(1H, d, J=8.2), 7.85(1H, m), 8.09(1H, m) |
| I-54 | 123.5-124.5 | 1.30-1.70(8H, m), 1.70-1.90(2H, m), 2.67(2H, s), 3.47(3H, s), 4.62(2H, s), 5.50(2H, s), 7.13(1H, dd, J=7.3, 1.0), 7.43-7.55(3H, m), 7.68(1H, d, J=8.2), 7.86(1H, m), 8.07(1H, m) |
| I-55 | 106-107 | 1.01(6H, d, J=6.9), 1.06(6H, d, J=6.9), 2.03(2H, sept, J=6.9), 2.79(2H, s), 3.44(3H, s), 4.69(2H, s), 5.48(2H, s), 7.08(1H, d, J=7.3), 7.41-7.53(3H, m), 7.66(1H, d, J=8.2), 7.85(1H, m), 8.08(1H, m) |
| I-56 | 120-121 | 1.34(3H, t, J=7.4), 1.30-1.70(10H, m), 2.62(2H, s), 2.96(2H, q, J=7.4), 3.92(2H, s), 7.00(1H, dd, J=7.3, 1.0), 7.40-7.52(3H, m), 7.64(1H, d, J=8.2), 7.84(1H, m), 8.11(1H, m) |

TABLE 9-continued

| Comp. No. | m.p. ° C. | NMR (CDCl₃) |
|---|---|---|
| I-57 | 101.5-102.5 | 1.00(6H, d, J=6.9), 1.01(6H, d, J=6.9), 1.32(3H, t, J=7.3), 1.97(2H, sept, J=6.9), 2.69(2H, s), 2.94(2H, q, J=7.3), 4.05(2H, s), 6.96(1H, dd, J=7.3, 1.0), 7.38-7.52(3H, m), 7.62(1H, d, J=8.2), 7.84(1H, m), 8.12(1H, m) |
| I-58 | 142-143 | 1.56-1.94(8H, m), 2.67(3H, s), 2.74(2H, s), 3.93(3H, s), 4.64(2H, s), 6.94(1H, dd, J=7.3, 1.0), 7.11-7.15(2H, m), 7.41(1H, m), 7.57(1H, d, J=8.2), 7.94(1H, d, J=8.9) |
| I-59 | 140.5-141.5 | 1.24-1.66(8H, m), 1.71-1.85(2H, m), 2.65(2H, s), 2.70(3H, s), 3.93(3H, s), 4.64(2H, s), 6.94(1H, dd, J=7.3, 1.0), 7.11-7.15(2H, m), 7.41(1H, m), 7.56(1H, d, J=7.9), 7.97(1H, d, J=8.9) |
| I-60 | 141-142 | 1.01(6H, d, J=6.9), 1.07(6H, d, J=6.9), 2.02(2H, sept, J=6.9), 2.69(3H, s), 2.76(2H, s), 3.93(3H, s), 4.74(2H, s), 6.89(1H, dd, J=7.3, .0), 7.11-7.15(2H, m), 7.40(1H, m), 7.54(1H, d, J=8.2), 7.97(1H, d, J=9.6) |
| I-61 | 121-122 | 1.35-1.86(10H, m), 2.60(2H, s), 2.69(3H, s), 4.61(2H, s), 5.16(2H, s), 7.06(1H, d, J=7.6), 7.23-7.47(7H, m), 7.55(1H, d, J=2.3), 7.61(1H, d, J=7.9), 7.78(1H, d, J=8.9) |
| I-62 | 88-91 | 1.34-1.85(10H, m), 2.67(2H, s), 2.69(3H, s), 4.64(2H, s), 5.07(1H, s), 7.06-7.15(2H, m), 7.26-7.37(2H, m), 7.60(1H, d, J=7.9), 7.77(1H, d, J=8.9) |

TABLE 10

| Comp. No. | m.p. ° C. | NMR (CDCl₃) |
|---|---|---|
| I-63 | 121-122 | 1.60-1.90(8H, m), 2.67(3H, s), 2.74(2H, s), 4.01(3H, s), 4.64(2H, s), 6.85(1H, d, J=8.1), 7.10(1H, dd, J=7.3, 1.0), 7.34-7.47(2H, m), 7.60(1H, d, J=8.6), 8.10(1H, d, J=8.2) |
| I-64 | 150-151 | 1.30-1.70(8H, m), 1.70-1.90(2H, m), 2.65(2H, s), 2.69(3H, s), 4.01(3H, s), 4.64(2H, s), 6.85(1H, d, J=7.6), 7.10(1H, dd, J=7.3, 1.0), 7.35-7.47(2H, m), 7.62(1H, d, J=8.2), 8.08(1H, d, J=8.2) |
| I-65 | 128-129 | 1.01(6H, d, J=6.9), 1.06(6H, d, J=6.9), 2.02(2H, sept, J=6.9), 2.69(3H, s), 2.76(2H, s), 4.01(3H, s), 4.74(2H, s), 6.84(1H, d, J=7.3), 7.05(1H, dd, J=7.3, 1.0), 7.34-7.46(2H, m), 7.63(1H, d, J=8.2), 8.07(1H, d, J=8.6) |
| I-66 | 142-143 | 1.50-1.80(8H, m), 2.34(3H, s), 2.75(2H, s), 3.95(2H, s), 4.00(3H, s), 6.84(1H, d, J=7.3), 7.00(1H, dd, J=7.3, 1.0), 7.34-7.45(2H, m), 7.62(1H, d, J=8.6), 8.06(1H, d, J=8.2) |
| I-67 | 125-126 | 1.30-1.70(10H, m), 2.37(3H, s), 3.92(2H, s), 4.00(3H, s), 6.85(1H, d, J=7.6), 7.00(1H, dd, J=7.3, 1.0), 7.35-7.45(2H, m), 7.67(1H, d, J=8.6), 8.06(1H, d, J=8.6) |
| I-68 | 152-153 | 0.99(6H, d, J=6.9), 1.01(6H, d, J=6.9), 1.97(2H, sept, J=6.9), 2.36(3H, s), 2.68(2H, s), 4.00(3H, s), 4.06(2H, s), 6.84(1H, d, J=6.9), 6.97(1H, dd, J=7.3, 1.0), 7.35-7.44(2H, m), 7.67(1H, d, J=8.6), 8.05(1H, d, J=8.2) |
| I-69 | 146-148 | 1.30-1.84(10H, m), 2.65(2H, s), 2.69(3H, s), 4.64(2H, s), 5.19(2H, s), 6.94(1H, d, J=7.3, 1.6), 7.19-7.23(2H, m), 7.31-7.55(7H, m), 7.98(1H, d, J=8.6) |
| I-70 | 144-145 | 1.01(6H, d, J=6.9), 1.07(6H, d, J=6.9), 2.02(2H, sept, J=6.9), 2.69(3H, s), 2.76(2H, s), 4.74(2H, s), 5.19(2H, s), 6.89(1H, dd, J=7.3, 1.0), 7.19-7.23(2H, m), 7.31-7.54(7H, m), 7.99(1H, d, J=8.6) |
| I-71 | 167-168 | 1.31-1.85(10H, m), 2.66(2H, s), 2.69(3H, s), 4.64(2H, s), 5.08(1H, s), 6.93(1H, dd, J=7.3, 1.3), 7.08(1H, dd, J=8.9, 2.6), 7.16(1H, d, J=2.6), 7.40(1H, m), 7.50(1H, d, J=8.2), 7.99(1H, d, J=8.9) |
| I-72 | | 1.31-1.85(10H, m), 2.67(2H, s), 2.70(3H, s), 3.20(3H, s), 4.64(2H, s), 7.12(1H, dd, J=7.3, 1.0), 7.39(1H, dd, J=9.2, 2.3), 7.52(1H, d, J=8.2), 7.66(1H, m), 7.76(1H, d, J=2.6), 8.18(1H, d, J=9.2) |
| I-73 | | 1.30-1.84(10H, m), 1.50(9H, s), 2.66(2H, s), 2.69(3H, s), 4.63(2H, s), 4.64(2H, s), 6.96(1H, dd, J=7.3, 1.0), 7.07(1H, d, J=2.6), 7.21(1H, dd, J=9.2, 2.6), 7.4(1H, m), 7.52(1H, d, J=8.2), 8.00(1H, d, J=9.2) |
| I-74 | 139-142(dec.) | 1.30-1.86(10H, m), 2.36(1H, s), 2.66(2H, s), 2.69(3H, s), 4.64(2H, s), 4.80(2H, s), 6.98(1H, dd, J=7.3, 1.0), 7.12-7.28(2H, m), 7.43(1H, m), 7.55(1H, d, J=8.2), 8.03(1H, d, J=9.2) |
| I-75 | 119-120 | 1.01(6H, d, J=6.9), 1.07(6H, d, J=6.9), 2.02(2H, sept, J=6.9), 2.69(3H, s), 2.77(2, s), 4.74(2H, s), 5.10(1H, brs), 6.88(1H, d, J=7.3), 7.07(1H, dd, J=8.9, 2.3), 7.15(1H, d, J=2.6), 7.38(1H, m), 7.48(1H, d, J=8.2), 7.99(1H, dd, J=8.9) |

TABLE 10-continued

| Comp. No. | m.p. ° C. | NMR (CDCl$_3$) |
|---|---|---|
| I-76 | | 1.02(6H, d, J=6.9), 1.07(6H, d, J=6.9), 2.02(2H, sept, J=6.9), 2.70(3H, s), 2.78(2H, s), 3.19(3H, s), 4.74(2H, s), 7.07(1H, dd, J=7.3, 1.0), 7.39(1H, dd, J=9.2, 2.6), 7.51(1H, m), 7.64(1H, d, J=8.2), 7.75(1H, d, J=3.3), 8.18(1H, d, J=9.2) |

TABLE 11

| Comp. No. | m.p. ° C. | NMR (CDCl$_3$) |
|---|---|---|
| I-77 | | 1.01(6H, d, J=6.9), 1.07(6H, d, J=6.9), 1.50(9H, s), 2.02(2H, sept, J=6.9), 2.69(3H, s), 2.76(2H, s), 4.63(2H, s), 4.74(2H, s), 6.91(1H, m), 7.07(1H, d, J=2.6), 7.20(1H, dd, J=9.2, 2.6), 7.40(1H, m), 7.51(1H, d, J=8.6), 7.99(1H, d, J=9.2) |
| I-78 | 150-152(dec.) | 1.01(6H, d, J=6.9), 1.06(6H, d, J=6.9), 2.02(2H, sept, J=6.9), 2.69(3H, s), 2.77(2H, s), 4.74(2H, s), 4.80(2H, s), 6.94(1H, d, J=6.6), 7.13(1H, d, J=2.6), 7.21(1H, dd, J=9.2, 2.6), 7.42(1H, m), 7.54(1H, d, J=7.9), 8.03(1H, d, J=8.9) |
| I-79 | 154-155 | 1.30-1.70(8H, m), 1.70-1.90(2H, m), 2.65(2H, s), 2.69(3H, s), 4.64(2H, s), 5.26(2H, s), 6.93(1H, d, J=7.3), 7.11(1H, dd, J=7.3, 1.0), 7.32-7.48(5H, m), 7.52-7.56(2H, m), 7.65(1H, d, J=8.6), 8.18(1H, d, J=8.2) |
| I-80 | 129-130 | 1.01(6H, d, J=6.9), 1.07(6H, d, J=6.9), 2.02(2H, sept, J=6.9), 2.69(3H, s), 2.76(2H, s), 4.75(2H, s), 5.26(2H, s), 6.92(1H, d, J=7.3), 7.06(1H, dd, J=7.3, 1.0), 7.33-7.47(5H, m), 7.52-7.56(2H, m), 7.65(1H, d, J=8.6), 8.17(1H, d, J=8.2) |
| I-81 | 69.5-71 | 1.30-1.70(8H, m), 1.70-1.90(2H, m), 2.66(2H, s), 2.69(3H, s), 4.64(2H, s), 5.54(1H, s), 6.85(1H, m), 7.10(1H, m), 7.30(1H, m), 7.46(1H, dd, J=8.2, 7.3), 7.63(1H, d, J=8.6), 8.01(1H, d, J=8.2) |
| I-82 | 110-112 | 1.01(6H, d, J=6.9), 1.06(6H, d, J=6.9), 2.02(2H, sept, J=6.9), 2.69(3H, s), 2.76(2H, s), 4.74(2H, s), 5.43(1H, brs), 6.84(1H, d, J=6.6), 7.05(1H, d, J=6.6), 7.29(1H, m), 7.45(1H, m), 7.64(1H, d, J=8.2), 7.99(1H, d, J=8.6) |
| I-83 | 166.5-167.5 | 1.30-1.70(8H, m), 1.70-1.90(2H, m), 2.68(2H, s), 2.70(3H, s), 3.22(3H, s), 4.65(2H, s), 7.18(1H, d, J=6.6), 7.47(1H, m), 7.53-7.60(2H, m), 7.95(1H, d, J=8.2), 8.06(1H, d, J=8.2) |
| I-84 | 128.5-129.5 | 1.02(6H, d, J=6.9), 1.07(6H, d, J=6.9), 2.02(2H, sept, J=6.9), 2.69(3H, s), 2.79(2H, s), 3.21(3H, s), 4.74(2H, s), 7.12(1H, d, J=7.3), 7.46(1H, t, J=7.9), 7.52-7.59(2H, m), 7.93(1H, d, J=8.6), 8.06(1H, d, J=8.6) |
| I-85 | 129-130 | 1.31-1.70(8H, m), 1.70-1.90(2H, m), 1.51(9H, s), 2.65(2H, s), 2.69(3H, s), 4.64(2H, s), 4.71(2H, s), 6.74(1H, d, J=7.6), 7.11(1H, d, J=6.6), 7.34(1H, t, J=8.1), 7.46(1H, dd, J=8.4, 7.4), 7.67(1H, d, J=8.2), 8.20(1H, d, J=8.2) |
| I-86 | 112-113 | 1.01(6H, d, J=6.9), 1.07(6H, d, J=6.9), 1.51(9H, s), 2.02(2H, sept, J=6.9), 2.69(3H, s), 2.76(2H, s), 4.70(2H, s), 4.74(2H, s), 6.73(1H, d, J=7.3), 7.06(1H, d, J=6.3), 7.34(1H, t, J=8.1), 7.45(1H, m), 7.67(1H, d, J=8.2), 8.18(1H, d, J=8.2) |
| I-87 | 153-154.5(dec.) | 1.30-1.70(8H, m), 1.70-1.90(2H, m), 2.65(2H, s), 2.69(3H, s), 4.64(2H, s), 4.86(2H, s), 6.78(1H, d, J=7.6), 7.13(1H, d, J=7.3), 7.36(1H, m), 7.48(1H, m), 7.71(1H, d, J=8.6), 8.15(1H, d, J=8.2) |
| I-88 | 156.5-158(dec.) | 1.01(6H, d, J=6.9), 1.06(6H, d, J=6.9), 2.01(2H, sept, J=6.9), 2.69(3H, s), 2.76(2H, s), 4.74(2H, s), 4.86(2H, s), 6.78(1H, d, J=7.6), 7.08(1H, d, J=6.6), 7.36(1H, m), 7.47(1H, m), 7.72(1H, d, J=8.6), 8.13(1H, d, J=8.2) |

TABLE 12

| Comp. No. | m.p. ° C. | NMR (CDCl$_3$) |
|---|---|---|
| I-89 | 131-132 | 1.31-1.88(10H, m), 1.57(9H, s), 2.65(2H, s), 2.74(3H, s), 4.60(2H, s), 4.65(2H, s), 7.07(1H, d, J=6.3), 7.27(1H, m), 7.34(1H, d, J=7.6), 7.47(1H, d, J=2.6), 7.61(1H, d, J=8.2), 7.78(1H, d, J=9.2) |
| I-90 | 124-130(dec.) | 1.31-1.90(10H, m), 2.65(2H, s), 2.73(3H, s), 4.64(2H, s), 4.77(2H, s), 7.09(1H, d, J=7.3), 7.26(1H, m), 7.36(1H, m), 7.51(1H, d, J=2.3), 7.63(1H, d, J=8.2), 7.81(1H, d, J=8.9) |

TABLE 12-continued

| Comp. No. | m.p. ° C. | NMR (CDCl₃) |
|---|---|---|
| I-91 | 130-131 | 1.31-1.87(10H, m), 2.67(2H, s), 2.71(3H, s), 3.16(3H, s), 4.65(2H, s), 7.16(1H, d, J=7.3), 7.40-7.53(2H, m), 7.69(1H, d, J=7.9), 7.91(1H, d, J=8.9), 8.10(1H, s) |
| I-92 | 155-156 | 1.31-1.87(10H, m), 2.68(2H, s), 2.73(3H, s), 4.66(2H, s), 4.87(2H, s), 7.11(1H, d, J=7.3), 7.19(1H, dd, J=8.9, 2.3), 7.40(1H, m), 7.55(1H, d, J=2.3), 7.64(1H, d, J=7.9), 7.82(1H, d, J=9.2) |
| I-93 | | 1.02(6H, d, J=6.9), 1.08(6H, d, J=6.9), 1.96-2.10(2H, m), 2.68(3H, s), 2.74(2H, s), 4.73(2H, s), 5.14(2H, s), 7.02(1H, d, J=7.3), 7.22-7.61(9H, m), 7.77(1H, d, J=8.9) |
| I-94 | | 1.01(6H, d, J=6.9), 1.07(6H, d, J=6.9), 2.03(2H, sept, J=6.9), 2.69(3H, s), 2.78(2H, s), 4.74(2H, s), 5.17(1H, brs), 7.02(1H, d, J=7.3), 7.13(1H, dd, J=8.9, 2.6), 7.29(1H, m), 7.37(1H, d, J=2.3), 7.58(1H, d, J=8.2), 7.76(1H, d, J=8.9) |
| I-95 | | 1.02(6H, d, J=6.9), 1.09(6H, d, J=6.9), 1.48(9H, s), 2.04(2H, sept, J=6.9), 2.73(3H, s), 2.76(2H, s), 4.59(2H, s), 4.75(2H, s), 7.02(1H, d, J=7.3), 7.23-7.34(2H, m), 7.45(1H, d, J=2.6), 7.59(1H, d, J=8.6), 7.77(1H, d, J=8.9) |
| I-96 | 148-150 | 1.02(6H, d, J=6.9), 1.08(6H, d, J=6.9), 2.02(2H, sept, J=6.9), 2.72(3H, s), 2.76(2H, s), 4.73(2H, s), 4.76(2H, s), 7.04(1H, d, J=7.3), 7.25(1H, m), 7.34(1H, m), 7.50(1H, d, J=2.6), 7.61(1H, d, J=7.9), 7.80(1H, d, J=8.9) |
| I-97 | 98-100 | 1.02(6H, d, J=6.9), 1.07(6H, d, J=6.9), 2.02(2H, sept, J=6.9), 2.71(3H, s), 2.79(2H, s), 3.15(3H, s), 4.74(2H, s), 7.11(1H, d, J=7.6), 7.39-7.51(2H, m), 7.67(1H, d, J=8.2), 7.90(1H, d, J=8.2), 8.09(1H, d, J=2.6) |
| I-98 | 156-157 | 1.36-1.68(10H, m), 2.35(3H, s), 2.69(2H, s), 3.95(2H, s), 7.08(1H, dd, J=7.3, 0.7), 7.57(1H, dd, J=8.9, 7.3), 7.81(1H, dd, J=8.9, 0.7) |
| I-99 | 110-111 | 1.00(6H, d, J=6.9), 1.03(6H, d, J=6.9), 1.98(2H, sept., J=6.9), 2.34(3H, s), 2.75(2H, s), 4.07(2H, s), 7.05(1H, dd, J=7.3, 1.0), 7.56(1H, dd, J=8.9, 7.3), 7.75(1H, dd, J=8.9, 1.0) |
| I-100 | 102.5-104 | 1.22-1.66(8H, m), 1.68-1.85(6H, m), 1.94-2.08(1H, m), 2.50-2.68(2H, m), 2.66(2H, s), 2.71-2.84(2H, m), 3.56(2H, t, J=5.9), 3.85-4.00(2H, m), 4.52(2H, s), 6.73(1H, d, J=7.6), 6.90(1H, d, J=7.6), 7.09(1H, t, J=7.6) |
| I-101 | 87-88.5 | 1.25-1.64(8H, m), 1.69-1.86(7H, m), 1.93-2.04(2H, m), 2.51-2.68(2H, m), 2.65(2H, s), 2.72-2.87(2H, m), 3.40-3.46(2H, m), 3.71-3.78(2H, m), 4.53(2H, s), 6.72(1H, d, J=7.6), 6.90(1H, d, J=7.6), 7.09(1H, t, J=7.6) |
| I-102 | 94.5-95.5 | 1.31-1.66(8H, m), 1.70-1.85(6H, m), 2.31(6H, s), 2.54-2.69(4H, m), 2.64(2H, s), 2.74-2.83(2H, m), 3.42(2H, t, J=7.6), 4.52(2H, s), 6.73(1H, d, J=7.6), 6.89(1H, d, J=7.6), 7.08(1H, t, J=7.6) |

TABLE 13

| Comp. No. | m.p. ° C. | NMR (CDCl₃) |
|---|---|---|
| I-103 | | 1.28-1.95(16H, m), 2.23(6H, s), 2.35-2.41(2H, m), 2.51-2.66(2H, m), 2.64(2H, s), 2.71-2.84(2H, m), 3.25-3.32(2H, m), 4.53(2H, s), 6.72(1H, d, J=7.6), 6.89(1H, d, J=7.6), 7.09(1H, t, J=7.6) |
| I-104 | | 1.01(6H, d, J=6.9), 1.07(6H, d, J=6.9), 1.97-2.12(4H, m), 2.64(3H, s), 2.78(2H, s), 2.87(2H, t, J=7.6), 2.95(2H, t, J=7.6), 4.66(2H, s), 6.70(1H, d, J=7.6), 7.02(1H, d, J=7.6), 7.13(1H, t, J=7.6) |
| I-105 | 118-119 | 0.99(6H, d, J=7.3), 1.01(6H, d, J=7.3), 1.85-2.12(4H, m), 2.31(3H, s), 2.73(2H, s), 2.86(2H, t, J=7.6), 2.94(2H, t, J=7.6), 3.97(2H, s), 6.66(1H, d, J=7.6), 7.00(1H, d, J=7.6), 7.12(1H, d, t=7.6) |
| I-106 | 105-106 | 0.93(6H, t, J=6.9), 1.10-1.60(8H, m), 2.07(2H, quint, J=7.6), 2.32(3H, s), 2.60(2H, s), 2.88(2H, t, J=7.6), 2.95(2H, t, J=7.6), 3.79(2H, s), 6.67(1H, d, J=7.6), 7.01(1H, d, J=7.6), 7.12(1H, t, J=7.6) |
| I-107 | 144-145 | 0.92(6H, t, J=6.9), 1.10-1.60(8H, m), 2.07(2H, quint, J=7.6), 2.62(2H, s), 2.64(3H, s), 2.88(2H, t, J=7.6), 2.95(2H, t, J=7.6), 4.48(2H, s), 6.73(1H, d, J=7.6), 7.04(1H, d, J=7.6), 7.14(1H, t, J=7.6) |
| I-108 | 165-168 | 1.30-1.71(10H, m), 2.30(3H, s), 2.66(2H, s), 3.86(2H, s), 4.27(2H, s), 4.27(2H, s), 6.52(1H, d, J=7.8), 6.67(1H, d, J=8.1), 6.80(1H, dd, J=8.1, 7.8) |
| I-109 | 148-150 | 1.30-1.65(8H, m), 1.70-1.85(2H, m) 2.63(3H, s), 2.67(2H, s), 4.28(2H, s), 4.28(2H, s), 4.58(2H, s), 6.60(1H, d, J=7.8), 6.70(1H, d, J=8.1), 6.82(1H, dd, J=8.1, 7.8) |
| I-110 | | 1.30-1.74(10H, m), 2.31(3H, s), 2.69(2H, s), 3.86(2H, s), 5.98(2H, s), 6.54(1H, d, J=7.8), 6.65(1H, d, J=7.8), 6.81(1H, t, J=7.8) |

TABLE 13-continued

| Comp. No. | m.p. ° C. | NMR (CDCl$_3$) |
|---|---|---|
| I-111 | 124-126 | 1.21-1.70(8H, m), 1.73-1.84(2H, m) 2.63(3H, s), 2.69(2H, s), 4.58(2H, s), 5.99(2H, s), 6.61(1H, d, J=8.1), 6.67(1H, d, J=7.8), 6.83(1H, dd, J=8.1, 7.8) |
| I-112 | 142-144 | 1.21-1.85(10H, m), 1.97(2H, m), 2.61(2H, m), 2.64(3H, s), 2.65(2H, s), 2.91(3H, s), 3.21(2H, t, J=5.9), 4.54(2H, s), 6.27(1H, d, J=7.9), 6.43(1H, d, J=7.9), 7.05(12H, t, J=7.9) |
| I-113 | 86.5-87.5 | 1.01(6H, d, J=6.9), 1.06(6H, d, J=6.9), 2.08(2H, sept, J=6.9), 2.69(3H, s), 2.78(2H, s), 4.73(2H, s), 6.97(1H, d, J=7.9), 7.50-7.65(3H, m), 8.09(1H, d, J=7.9), 8.26(1H, d, J=7.9) |
| I-114 | 111.5-112.5 | 1.00(6H, d, J=6.9), 1.01(6H, d, J=6.9), 1.97(2H, sept, J=6.9), 2.37(3H, s), 2.71(2H, s), 4.06(2H, s), 6.88(1H, d, J=7.9), 7.49-7.65(3H, m), 8.12(1H, m), 8.26(1H, m) |
| I-115 | 178-179.5 | 1.39-1.79(10H, m), 2.70(3H, s), 2.71(2H, s), 4.66(2H, s), 7.12(1H, d, J=7.9), 7.60(1H, m), 7.75(1H, m), 8.15(1H, m), 8.34(1H, d, J=7.9), 8.74(1H, d, J=7.9) |
| I-116 | 135-136 | 1.47-1.59(10H, m), 2.38(3H, s), 2.69(2H, s), 3.95(2H, s), 7.02(1H, d, J=8.6), 7.60(1H, m), 7.75(1H, m), 8.19(1H, d, J=8.6), 8.33(1H, d, J=8.6), 8.75(1H, d, J=8.6) |

TABLE 14

| Comp. No. | m.p. ° C. | NMR (CDCl$_3$) |
|---|---|---|
| I-117 | 127.5-128.5 | 1.36-1.69(10H, m), 2.38(3H, s), 2.65(2H, s), 3.16(3H, s), 3.93(2H, s), 7.04-7.08(1H, m), 7.40-7.51(2H, m), 7.66(1H, d, J=8.2), 7.90(1H, d, J=8.9), 8.11(1H, d, J=2.3) |
| I-118 | 130.5-131.5 | 1.37-1.70(10H, m), 1.48(9H, s), 2.42(3H, s), 2.61(2H, s), 3.93(2H, s), 4.63(2H, s), 6.94-6.98(1H, m), 7.22-7.33(2H, m), 7.55(1H, d, J=2.6), 7.59(1H, d, J=8.2), 7.77(1H, d, J=8.9) |
| I-119 | 155.5-156.5 | 1.32-1.68(10H, m), 2.39(3H, s), 2.60(2H, s), 3.92(2H, s), 4.77(2H, s), 6.96-7.00(1H, m), 7.22-7.36(2H, m), 7.55-7.61(1H, m), 7.77(1H, d, J=8.9) |
| I-120 | 127-128 | 1.35-1.69(10H, m), 2.42(3H, s), 2.65(2H, s), 3.94(2H, s), 4.89(2H, s), 6.99-7.03(1H, m), 7.19(1H, dd, J=8.9, 2.6), 7.34-7.40(1H, m), 7.59-7.65(2H, m), 7.81(1H, d, J=8.9) |
| I-121 | 131-132 | 1.02(6H, d, J=6.9), 1.06(6H, d, J=6.9), 2.01(2H, sept, J=6.9), 2.69(3H, s), 2.82(2H, s), 4.73(2H, s), 7.06(1H, d, J=8.2), 7.60(1H, m), 7.75(1H, m), 8.16(1H, d, J=7.9), 8.34(1H, d, J=8.2), 8.75(1H, d, J=8.2) |
| I-122 | 150-151 | 1.01(6H, d, J=6.9), 1.02(6H, d, J=6.9), 1.99(2H, sept, J=6.9), 2.37(3H, s), 2.75(2H, s), 4.08(2H, s), 6.99(1H, d, J=8.2), 7.60(1H, m), 7.74(1H, m), 8.19(1H, d, J=8.2), 8.33(1H, d, J=8.2), 8.75(1H, d, J=8.6) |
| I-123 | 173-175 | 1.01(6H, d, J=6.9), 1.07(6H, d, J=6.9), 2.02(2H, sept, J=6.9), 2.32(3H, s), 2.69(3H, s), 2.78(2H, s), 4.73(2H, s), 7.05(1H, d, J=7.9), 7.20-7.58(3H, m), 7.84(1H, m), 8.11(1H, d, J=7.9) |
| I-124 | | 1.01(6H, d, J=6.9), 1.07(6H, d, J=6.9), 2.04(2H, sept, J=6.9), 2.68(3H, s), 2.77(2H, s), 4.09(2H, brs), 4.73(2H, s), 6.76(1H, d, J=7.9), 6.94(1H, d, J=7.9), 7.44-7.52(2H, m), 7.83(1H, m), 8.10(1H, m) |
| I-125 | 183-184 | 1.02(6H, d, J=6.9), 1.09(6H, d, J=6.9), 2.02(2H, sept, J=6.9), 2.69(3H, s), 2.79(2H, s), 3.00(3H, s), 4.74(2H, s), 6.70(1H, s), 7.06(1H, d, J=7.9), 7.52-7.65(3H, m), 8.06(1H, d, J=7.9), 8.14(1H, d, J=7.9) |
| I-126 | 225-226 | 1.01(6H, d, J=6.9), 1.06(6H, d, J=6.9), 2.01(2H, sept, J=6.9), 2.68(3H, s), 2.79(2H, s), 3.51(6H, s), 4.74(2H, s), 7.07(1H, d, J=7.9), 7.48-7.68(3H, m), 8.05(1H, d, J=7.9), 8.11(1H, d, J=7.9) |
| I-127 | 153-154 | 1.02(6H, d, J=6.9), 1.07(6H, d, J=6.9), 2.03(2H, sept, J=6.9), 2.70(3H, s), 2.79(2H, s), 4.75(2H, s), 7.11(1H, d, J=8.2), 7.49-7.61(5H, m), 7.89-8.17(5H, m) |
| I-128 | 140-141 | 0.95(6H, t, J=6.9), 1.21-1.53(8H, m), 2.39(3H, s), 2.64(2H, s), 3.89(2H, s), 7.01(1H, d, J=8.2), 7.60(1H, m), 7.75(1H, m), 8.19(1H, d, J=8.2), 8.33(1H, d, J=8.2), 8.75(1H, d, J=8.2) |
| I-129 | 171.5-172.5 | 0.92(6H, t, J=6.9), 1.26-1.61(8H, m), 2.67(2H, s), 2.7.0(3H, s), 4.57(2H, s), 7.10(1H, d, J=8.2), 7.60(1H, m), J=7.76(1H, m), 8.15(1H, d, J=7.9), 8.34(1H, d, J=8.2), 8.74(1H, d, J=8.2) |

TABLE 15

| Comp. No. | m.p. ° C. | NMR (CDCl₃) |
|---|---|---|
| I-130 | 135-136 | 1.42-1.82(10H, m), 2.66(2H, s), 2.68(3H, s), 4.11(2H, brs), 4.62(2H, s), 6.77(1H, d, J=7.9), 7.00(1H, d, J=7.9), 7.45-7.53(2H, m), 7.83(1H, m), 8.12(1H, m) |
| I-131 | 133-134.5 | 0.92(6H, t, J=6.9), 1.18-1.59(8H, m), 2.62(2H, s), 2.69(3H, s), 4.10(2H, brs), 4.54(2H, s), 6.77(1H, d, J=7.9), 6.99(1H, d, J=7.9), 7.44-7.52(2H, m), 7.83(1H, m), 8.11(1H, m) |
| I-132 | 219-220 | 1.30-1.78(10H, m), 2.18(3H, s), 2.64(3H, s), 2.78(2H, s), 4.60(2H, s), 7.08(1H, d, J=8.2), 7.53-7.65(3H, m), 8.02-8.09(2H, m), 9.90(1H, s) |
| I-133 | 139-140 | 1.25-1.88(10H, m), 2.67(2H, s), 2.69(3H, s), 4.64(2H, s), 5.26(2H, s), 6.88(1H, d, J=7.9), 7.03(1H, d, J=7.9), 7.36-7.56(7H, m), 8.06(1H, m), 8.36(1H, m) |
| I-134 | 104.5-105.5 | 1.01(6H, d, J=6.9), 1.07(6H, d, J=6.9), 2.03(2H, sept, J=6.9), 2.69(3H, s), 2.77(2H, s), 4.74(2H, s), 5.25(2H, s), 6.87(1H, d, J=8.3), 6.97(1H, d, J=8.3), 7.33-7.55(7H, m), 8.06(1H, m), 8.34(1H, m) |
| I-135 | 142-143 | 1.28-1.68(8H, m), 1.71-1.87(2H, m), 2.66(2H, s), 2.69(3H, s), 4.29(2H, s), 5.28(1H, s), 6.81(1H, d, J=7.9), 6.97(1H, d, J=7.9), 7.48-7.55(2H, m), 8.07(1H, m), 8.18(1H, m) |
| I-136 | 166-167 | 1.30-1.67(8H, m), 1.72-1.89(2H, m), 2.69(5H, s), 3.21(3H, s), 4.64(2H, s), 7.08(1H, d, J=8.2), 7.50-7.63(3H, m), 8.08-8.14(2H, m) |
| I-137 | 173-174 | 1.20-1.68(11H, m), 1.72-1.89(2H, m), 2.66(2H, s), 2.69(3H, s), 4.21(2H, q, J=7.3), 4.63(2H, s), 6.78(1H, d, J=8.2), 7.02(1H, d, J=8.2), 7.45-7.53(2H, m), 8.04(1H, m), 8.31(1H, m) |
| I-138 |  | 1.29-1.68(8H, m), 1.73-1.87(2H, m), 2.67(2H, s), 2.70(3H, s), 4.64(2H, s), 4.97(2H, s), 6.92(1H, d, J=7.9), 7.04(1H, d, J=7.9), 7.50-7.60(2H, m), 8.07(1H, m), 8.21(1H, m) |
| I-139 |  | 1.01(6H, d, J=6.9), 1.07(6H, d, J=6.9), 2.03(2H, sept, J=6.9), 2.69(3H, s), 2.77(2H, s), 4.73(2H, s), 5.26(2H, s), 6.80(1H, d, J=7.9), 6.91(1H, d, J=6.9), 7.47-7.56(2H, m), 8.05(1H, m), 8.18(1H, m) |
| I-140 | 139-140 | 1.25-1.87(10H, m), 2.67(2H, s), 2.70(3H, s), 4.64(2H, s), 7.02(1H, m), 7.13(1H, m), 7.55(2H, m), 8.09(2H, m) |
| I-141 | 111-112 | 1.31-1.75(10H, m), 2.38(3H, s), 2.64(2H, s), 3.92(2H, s), 6.89(1H, m), 7.10(1H, m), 7.55(2H, m), 8.10(2H, m) |
| I-142 | 118-119 | 1.01(6H, d, J=6.9), 1.07(6H, d, J=6.9), 2.02(2H, sept, J=6.9), 2.69(3H, s), 2.77(2H, s), 4.73(2H, s), 6.96(1H, dd, J=7.3, 4.9), 7.11(1H, dd, J=10.6, 8.2), 7.55(2H, m), 8.08(2H, m) |
| I-143 | 109-110 | 1.00(6H, d, J=6.9), 1.02(6H, d, J=6.9), 1.97(2H, sept, J=6.9), 2.37(3H, s), 2.70(2H, s), 4.06(2H, s), 6.88(1H, dd, J=7.6, 4.6), 7.09(1H, dd, J=10.2, 7.9), 7.55(2H, m), 8.07(2H, m) |

TABLE 16

| Comp. No. | m.p. ° C. | NMR (CDCl₃) |
|---|---|---|
| I-144 | 164-165 | 1.31-1.88(10H, m), 2.69(5H, s), 4.56(2H, s), 7.11(1H, d, J=7.9), 7.60(1H, m), 7.72(1H, m), 7.90(1H, d, J=7.9), 8.13(1H, d, J=8.2), 8.25(1H, d, J=7.9) |
| I-145 | 137-138.5 | 1.01(6H, d, J=6.9), 1.06(6H, d, J=6.9), 2.01(2H, sept, J=6.9), 2.69(3H, s), 2.80(2H, s), 4.73(2H, s), 7.06(1H, d, J=7.9), 7.59(1H, m), 7.71(1H, m), 7.87(1H, d, J=7.6), 8.13(1H, d, J=8.2), 8.24(1H, d, J=8.6) |
| I-146 | 131.5-133 | 1.28-1.62(8H, m), 1.70-1.85(2H, m), 1.99(1H, t, J=6.3), 2.67(2H, s), 3.61(2H, t, J=5.9), 3.97(2H, dt, J=6.3, 5.9), 4.62(2H, s), 7.11(1H, d, J=7.6), 7.42-7.54(3H, m), 7.68(1H, d, J=8.2), 7.83-7.88(1H, m), 8.02-8.06(1H, m) |
| I-147 | 90-92 | 1.24-1.65(8H, m), 1.71-1.86(2H, m), 1.99(1H, t, J=5.9), 2.68(2H, s), 3.61(2H, t, J=5.9), 3.97(2H, q, J=5.9), 4.61(2H, s), 7.01-7.17(2H, m), 7.50-7.61(2H, m), 8.03-8.12(2H, m) |
| I-148 | 153-154 | 1.01(6H, d, J=6.9), 1.02(6H, d, J=6.9), 1.98(2H, sept, J=6.9), 2.37(3H, s), 2.73(2H, s), 4.07(2H, s), 6.99(1H, d, J=7.9), 7.59(1H, m), 7.70(1H, m), 7.86(1H, d, J=7.9), 8.16(1H, d, J=8.2), 8.23(1H, d, J=8.2) |
| I-149 | 124.5-125.5 | 1.25-1.87(11H, m), 1.97-2.08(2H, m), 2.66(2H, s), 3.45-3.52(2H, m), 3.74-3.82(2H, m), 4.63(2H, s), 7.10(1H, d, J=7.3), 7.42-7.54(3H, m), 7.67(1H, d, J=8.6), 7.83-7.88(1H, m), 8.05-8.09(1H, m) |
| I-150 | 111.5-113 | 1.30-1.67(8H, m), 1.71-1.86(2H, m), 2.33(6H, s), 2.65(2H, s), 2.69(2H, t, J=7.6), 3.48(2H, t, J=7.6), 4.62(2H, s), 7.10(1H, d, J=7.3), 7.42-7.54(3H, m), 7.67(1H, d, J=8.2), 7.83-7.87(1H, m), 8.08-8.12(1H, m) |

TABLE 16-continued

| Comp. No. | m.p. ° C. | NMR (CDCl$_3$) |
|---|---|---|
| I-151 | 105-106 | 1.31-1.65(8H, m), 1.73-1.86(2H, m), 1.94(2H, quint., J=7.6), 2.24(6H, s), 2.41(2H, t, J=7.6), 2.65(2H, s), 3.35(2H, t, J=7.6), 4.62(2H, s), 7.09(1H, d, J=7.3), 7.42-7.53(3H, m), 7.67(1H, d, J=8.2), 7.83-7.87(1H, m), 8.08-8.11(1H, m) |

The above compounds of the present invention were examined as shown below.

Example 1

Experiments for Human CB Receptor (CBR) Binding Inhibition

The crude membrane fractions were then prepared from the CB1R or CB2R-expressing CHO cells. Receptor binding assay was performed by incubating the membranes with each test compound and 38,000 dpm [$^3$H]CP55940 (at a final concentration of 0.5 nM: PerkinElmer Life & Analytical Sciences) in the assay buffer (50 mM Tris-HCl, 1 nM EDTA, 3 mM MgCl$_2$, pH 7.4) containing 0.5% bovine serum albumin (BSA) for 2 hr at 25° C. The incubation mixture was filtered through 1% polyethylenimine (PEI)-treated GF/C glass filter and washed with 50 mM Tris-HCl (pH 7.4) containing 0.1% BSA. The radioactivity was then counted with a liquid scintillation counter. Nonspecific binding was determined in the presence of 10 μM WIN55212-2 (a CBR agonist described in the patent U.S. Pat. No. 508,122, Sigma), and the specific binding was calculated by subtracting the nonspecific binding from the total binding. The IC$_{50}$ value for each test compound was determined as the concentration at which 50 % of the specific binding was inhibited. As a consequence of these studies, the Ki values of each test compound were determined from the IC$_{50}$ value and the Kd vale of [$^3$H]CP55940.

TABLE 17

| Compound No. | CB receptor binding inhibition Ki (nM) | |
|---|---|---|
| | CB1 | CB2 |
| I-6 | 15.0 | 0.2 |
| I-14 | 16.0 | 1.6 |
| I-22 | 20.0 | 1.5 |
| I-23 | 29.6 | 6.0 |
| I-25 | 42.5 | 1.0 |
| I-27 | 13.0 | 0.3 |
| I-28 | 31.4 | 4.8 |
| I-29 | 6.0 | 1.7 |
| I-33 | 20.7 | 1.2 |
| I-43 | 21.4 | 11.3 |
| I-77 | 35.0 | 1.5 |
| I-105 | 23 | 2.2 |
| I-108 | 21 | 0.7 |
| I-109 | 30 | 1 |
| I-113 | 10 | 0.9 |
| I-114 | 25 | 5.9 |
| I-140 | 59 | 0.8 |
| I-142 | 20 | 1.2 |
| I-143 | 29 | 1.4 |
| I-144 | 54 | 1 |

Example 2

Inhibition Experiments for CBR-mediated Suppression of cAMP Synthesis

The CHO cells expressing human CB1R or CB2R were incubated with test compounds for 15 min. After the incubation, 4 μM forskolin (Sigma) was added and the cells were incubated for 20 min. The reaction was stopped by the addition of 1N HCl and the amount of cAMP in the cell supernatant was measured using an Cyclic AMP kit (CIS bio international) according to the manufacture's protocol. The cAMP amount increased by forskolin compared to that in the absence of forskolin was defined as 100%, and the IC$_{50}$ value of each test compound was determined as the concentration at which 50% of the forskolin-stimulated cAMP synthesis was inhibited.

TABLE 18

| Compound No. | Inhibition of cAMP synthesis IC$_{50}$ (nM) | |
|---|---|---|
| | CB1 | CB2 |
| I-6 | 3.2 | 0.2 |
| I-10 | n.t. | 0.2 |
| I-14 | 4 | 2.7 |
| I-23 | 10.4 | 1.7 |
| I-27 | 8.1 | n.t. |
| I-29 | 17.5 | n.t. |
| I-105 | 25 | n.t. |
| I-113 | 13 | 1.5 |
| I-114 | 24 | 48 |
| I-140 | 27 | n.t. |
| I-142 | 14 | n.t. |
| I-143 | 35 | n.t. |
| I-144 | 52 | n.t. | n.t.: not tested

Example 3

Inhibitory Effect Against Formalin-induced Hyperalgesia in ICR Mice

The inhibitory effects of the compounds of the present invention against formalin-induced hyperalgesia were examined in male ICR mice (5 W). Test compounds were dissolved in sesami oil and applied orally 2 h prior to the subcutaneous formalin injection (2% 20 μL) into the right hind paw. In this experiment, observation period was set to 30 min and divided into two parts, the first 5 minutes immediately after the formalin injection (first phase) and 10 to 30 min minutes after the formalin injection (second phase). The strength for pain sensation was evaluated by the total time for licking and biting behavior. The inhibitory effect of the test compounds on such behavior was evaluated and the ED$_{50}$ value was calculated.

TABLE 19

| | Oral administration | |
|---|---|---|
| | Inhibitory effect against formalin-induced hyperalgesia ($ED_{50}$) | |
| Compound | First phase (mg/kg) | Second phase (mg/kg) |
| I-6 | 2.5 | 4.0 |
| I-14 | 5.2 | 3.1 |
| I-23 | 1.5 | 1.0 |
| I-29 | 3.6 | 3.5 |

Experimental Example 4

Inhibitory Effect on Compound 48/80-Induced Pruritus in ICR Strain Mice

The experiment was carried out by the method of Inagaki et al. (Eur J Pharmacol 1999;367:361-371) with some modifications. Briefly, the back of female ICR strain mice was clipped, and compound 48/80 (3 µg/50 µL/site) was injected intradermally to elicit the response. The number of scratching behavior to the injection site by hind paws, which was observed immediately after the injection, was counted for 30 min. Test compounds, dissolved in sesame oil, were orally administered once. After the injection of compound 48/80 at pre-determine time when the maximal plasma concentration of the compound was obtained. The inhibitory effect against pruritus was evaluated by comparing the number of scratching in the compound-administered group with that in the vehicle-administered group, and then ED50 value was calculated.

I-23 demonstrated a potent anti-pruritic effect with ED50 value of 0.54 mg/kg.

Experimental Example 5

Bronchodilating Effect in Guinea Pigs

Under urethane anesthesia (1.4 g/kg, i.p.), acetylcholine (ACh) was intravenously injected to guinea pigs by increasing doses of ACh every 5 min, then bronchoconstrictor response observed immediately after each ACh injection was measured by the method of Konzett & Rössler with some modifications. Briefly, trachea of guinea pigs was incised and a cannula was attached to lung side. An artificial respirator (SN-480-7, Shinano) was connected to the cannula, and then a fixed amount of air (tidal volume: 4 mL, ventilation frequency: 60 times/min) continuously insufflated to maintain respiration. The insufflation pressure overflowed from inhalation tube was monitored by a pressure transducer (TP-400T, Nihon Kohden) and recorded on a recorder (WT-645G, Nihon Kohden) through a carrier amplifier (AP-601G, Nihon Kohden). Test compounds were administered orally 1 h before ACh injection, then the effect on the dose-response curve of ACh was examined. Statistical significance was analyzed concerning broncohdilating effect in guinea pigs.

Formulation Example

The following formulation examples 1 to 8 are provided to further illustrate formulation example and are not to be construed as limiting the scope of the present invention. The term "an active ingredient" means a compound of the present invention, a tautomer, a prodrug, a pharmaceutical acceptable salt, or a solvate thereof.

Formulation Example 1

Hard gelatin capsule are prepared using the following ingredients.

| | | Dosage (mg/capsule) |
|---|---|---|
| Ingredients | An actve ingredient | 250 |
| | Starch (dry) | 200 |
| | Magnesium stearate | 10 |
| | Total | 460 mg |

Formulation 2

Tablets are prepared using the following ingredients.

| Ingredients | Dosage (mg/tablet) |
|---|---|
| An actve ingredient | 250 |
| Cellulose (microcrystalline) | 400 |
| Silicon dioxide (fume) | 10 |
| Stearic acid | 5 |
| Total | 665 mg |

These ingredients are mixed and condensed to prepare tablets of 665 mg.

Formulation 3

Aerosol solution are prepared using the following ingredients.

| Ingredients | Weight |
|---|---|
| An actve ingredient | 0.25 |
| Ethanol | 25.75 |
| Properanto 22 (chlorodifluorometahne) | 74.00 |
| Total | 100.00 |

An active ingredient and ethanol are mixed, and the mixture is added into a part of properanto 22, cooled at −30° C., transferred to packing equipment. The amount needed is provided to stainless steel vessel, diluted with residual properanto 22. The bubble unit is insalled to vessel.

Formulation 4

Tablets containing an active ingredients 60 mg are prepared as follows.

| Ingredients | | |
|---|---|---|
| | An active ingredient | 60 mg |
| | Starch | 45 mg |
| | Microcrystal cellulose | 35 mg |
| | Polyvinylpyrrolidone (10% aqueous solution) | 4 mg |
| | Carboxymethyl starch sodium salt | 4.5 mg |
| | Magnesium stearate | 0.5 mg |
| | Talc | 1 mg |
| | | 150 mg |

An active ingredient, Starch, and cellulose are made pass through a No. 45 mesh U.S. sieve and then mixed sufficiently. The resulting mixture is mixed with a polyvinylpyrrolidone aqueous solution, made pass through a No. 14 mesh U.S. sieve. The obtained granule is dried at 50° C., made pass through a No. 18 mesh U.S. sieve. To the granule are added carboxymethyl starch-Na, Magnesium stearate, and talc made pass through a No. 60 mesh U.S. sieve, and the mixture was mixed. The mixed powder is compressed by tableting equipment to yield tablets of 150 mg.

Formulation 5

Capsules containing an active ingredients 80 mg are prepared as follows.

| Ingredients | An active ingredient | 80 mg |
| | Starch | 59 mg |
| | Microcrystal cellulose | 59 mg |
| | Magnesium stearate | 2 mg |
| | Total | 200 mg |

An active ingredient, Starch, cellulose, and magnesium stearate are mixed, made pass through a No. 45 mesh U.S. sieve, and then packed to hard gelatin capsules at amount of 200 mg/capsule.

Formulation 6

Suppository containing an active ingredient 225 mg are prepared as follows.

| Ingredients | An active ingredient | 225 mg |
| | Saturated fattyacid glyceride | 2000 mg |
| | Total | 2225 mg |

An active ingredient is made pass through a No. 60 mesh U.S. sieve, suspended in saturated fattyacid glyceride dissolved by heating at a minimum of necessity. The mixture is cooled in the mould of 2 mg.

Formulation 7

Suspension containing an active ingredient 50 mg are prepared as follows.

| Ingredients | An active ingredient | 50 mg |
| | Carboxymethylcellulose sodium salt | 50 mg |
| | Syrupus | 1.25 mL |
| | Benzoic acid solution | 0.10 mL |
| | Aroma chemical | q.v. |
| | Pigmentum | q.v. |
| | Water | |
| | Total | 5 mL |

An active ingredient is made pass through a No. 60 mesh U.S. sieve, mixed with carboxymethylcellulose sodium salt and to prepare smoothly paste. To the mixture are benzoic acid solution and syrupus which are diluted with a part of water, and the mixture is stirred. To the mixture is residual water to prepare necessary volume.

Formulation 8

Intravenous formulations are prepared as follows.

| Ingredients | An active ingredient | 100 mg |
| | Saturated fattyacid glyceride | 1000 ml |

Usually a solution of ingredients above described is administered intravenously to a patient by the speed of 1 ml/min.

INDUSTRIAL APPLICABILITY

It was found that 2-naphthylimino-1,3-thiazine derivatives having cannabinoid receptor agonistic acitivity exibit the effect as an analgesics, a treating agent for algesic, an antipruritics or a bronchodilator.

The invention claimed is:

1. A compound represented by the formula (I):

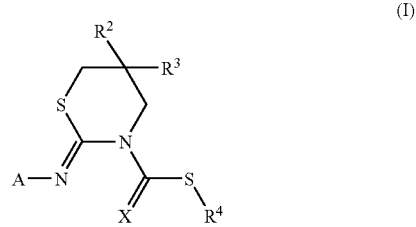

(I)

wherein $R^2$ and $R^3$ are the same or different and each is C2-C4 alkyl, C2-C4 alkenyl, C1-C4 alkoxyC1-C4 alkyl, optionally substituted aminoC1-C4 alkyl, or C3-C6 cycloalkylC1-C4 alkyl; or $R^2$ and $R^3$ are taken together with the adjacent carbon atom to form an optionally substituted 5 to 8 membered non-aromatic carbocyclic ring or an optionally substituted 5 to 8 membered non-aromatic heterocyclic ring;

$R^4$ is C1-C6 alkyl, hydroxyC1-C6alkyl, optionally substituted aminoC1-C6alkyl, or C1-C6 alkoxyC1-C6 alkyl;

X is an oxygen atom or a sulfur atom;

A is a group of the formula:

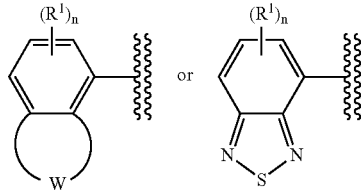

wherein $R^1$ is, same or different, alkyl, alkoxy, alkylthio, optionally substituted amino, optionally substituted aryl, optionally substituted aryloxy, optionally substituted aralkyloxy, cycloalkyl, a halogen atom, hydroxy, nitro, haloalkyl, haloalkoxy, optionally substituted carbamoyl, carboxy, alkoxycarbonyl, alkylsulfinyl, alkylsulfonyl, alkoxylalkyl, alkylthioalkyl, optionally substituted aminoalkyl, alkoxyiminoalkyl, alkoxyalkoxy, alkylthioalkoxy, alkoxycarbonylalkoxy, carboxyalkoxy, alkylsulfonyloxy, optionally substituted heteroaryl, an optionally substituted non-aromatic heterocyclic group, cyano, cyanoalkoxy, or a group of the formula: —C(=O)—$R^H$ wherein $R^H$ is a hydrogen atom, alkyl, optionally substituted aryl, or an optionally substituted non-aromatic heterocyclic group;

W is —CH$_2$CH$_2$CH$_2$—, —CH$_2$CH$_2$CH$_2$CH$_2$—, —OCH$_2$O—, —OCH$_2$CH$_2$O—, —N(CH$_3$)CH$_2$CH$_2$CH$_2$—, or —CH═CH—CH═CH—;

n is an integer of 0 to 7;

wherein the optionally substituted amino is non-substituted amino, C1-C4 alkylamino, (C1-C4 alkyl)carbonylamino, aryl carbonylamino, N—(C1-C4 alkyl)carbonyl-C1-C4 alkylamino, aralkylamino, C1-C4 alkylsulfonylamino, C2-C4 alkenyloxycarbonylamino, (C1-C4 alkoxy)carbonylamino, C2-C4 alkenylamino, arylcarbonylamino, or heteroarylcarbonylamino, the substituent of optionally substituted carbamoyl is selected from the group consisting of alkyl and acyl, and, the substituent of non-aromatic carbocyclic ring, non-aromatic heterocyclic ring, aryl, aryloxy, aralkyloxy, heteroaryl, and a non-aromatic heterocyclic group is selected from the group consisting of hydroxy, carboxy, a halogen atom, haloalkyl, haloalkoxy, alkyl, alkenyl, formyl, acyl, alkynyl, cycloalkyl, alkoxy, alkoxycarbonyl, nitro, nitroso, oxo, optionally substituted amino, azido, aryl, aryloxy, cyano, isocyano, isocyanato, thiocyanato, isothiocyanato, mercapto, alkylthio, alkylsulfonyl, arylsulfonyl, optionally substituted carbamoyl, sulfamoyl, formyloxy, haloformyl, oxalo, thioformyl, thiocarboxy, dithiocarboxy, thiocarbamoyl, sulfino, sulfo, sulfoamino, hydrazino, ureido, amidino, guanidino, formyloxy, thioxo, alkoxyalkoxy, and alkylthioalkoxy, a pharmaceutically acceptable salt thereof.

2. The compound according to claim 1 wherein R$^2$ and R$^3$ are taken together with the adjacent carbon atom to form an optionally substituted 5 to 6 membered carbocyclic ring, a pharmaceutically acceptable salt thereof.

3. A compound of the formula (II):

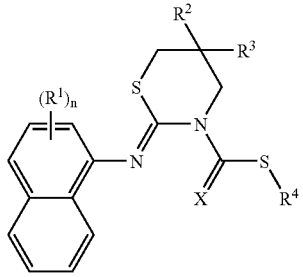

(II)

wherein R$^1$ is, same or different, alkyl, alkoxy, optionally substituted amino, a halogen atom, hydroxy, haloalkyl, haloalkoxy, cyano, or alkoxycarbonylalkoxy;

each of R$^2$ and R$^3$ is, same or different, C2-C4 alkyl; or

R$^2$ and R$^3$ are taken together with the adjacent carbon atom to form 5 to 6 membered cycloalkane;

R$^4$ is C1-C6 alkyl;

X is an oxgen atom or a sulfur atom;

n is an integer of 0 to 7;

wherein the optionally substituted amino is non-substituted amino, C1-C4 alkylamino, (C1-C4 alkyl)carbonylamino, aryl carbonylamino, N—(C1-C4 alkyl)carbonyl-C1-C4 alkylamino, aralkylamino, C1-C4 alkylsulfonylamino, C2-C4 alkenyloxycarbonylamino, (C1-C4 alkoxy)carbonylamino, C2-C4 alkenylamino, arylcarbonylamino, or heteroarylcarbonylamino, a pharmaceutically acceptable salt thereof.

4. The compound according to claim 3 wherein R$^1$ is a fluorine atom, a chlorine atom, dimethylamino, cyano, or t-butoxycarbonylmethoxy, a pharmaceutically acceptable salt thereof.

5. The compound according to claim 3 or 4 wherein n is 0 or 1, a pharmaceutically acceptable salt thereof.

6. A compound of the formula (II):

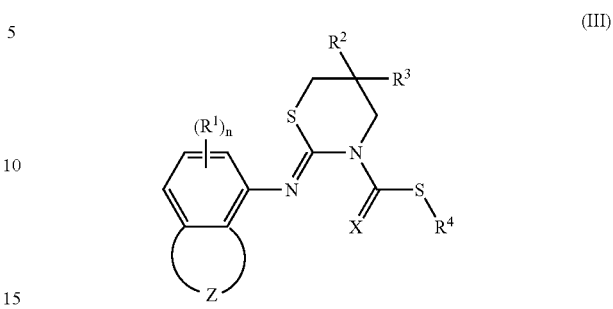

(III)

wherein R$^1$ is, same or different, alkyl, alkoxy, optionally substituted amino, a halogen atom, hydroxy, haloalkyl, haloalkoxy, cyano, or alkoxycarbonylalkoxy;

each of R$^2$ and R$^3$ is, same or different, C2-C4 alkyl; or

R$^2$ and R$^3$ are taken together with the adjacent carbon atom to form 5 to 6 membered cycloalkane;

R$^4$ is C1-C6alkyl;

X is an oxygen atom or a sulfur atom;

Z is —CH$_2$CH$_2$CH$_2$—, —CH$_2$CH$_2$CH$_2$CH$_2$—, or —OCH$_2$CH$_2$O—;

n is an integer of 0 to 3;

wherein the optionally substituted amino is non-substituted amino, C1-C4 alkylamino, (C1-C4 alkyl)carbonylamino, aryl carbonylamino, N—(C1-C4 alkyl)carbonyl-C1-C4 alkylamino, aralkylamino, C1-C4 alkylsulfonylamino, C2-C4 alkenyloxycarbonylamino, (C1-C4 alkoxy)carbonylamino, C2-C4 alkenylamino, arylcarbonylamino, or heteroarylcarbonylamino, a pharmaceutically acceptable salt thereof.

7. The compound according to claim 6 wherein Z is —CH$_2$CH$_2$CH$_2$—or —CH$_2$CH$_2$CH$_2$CH$_2$—, a pharmaceutically acceptable salt thereof.

8. The compound according to claim 6 wherein Z is —OCH$_2$CH$_2$O—, a pharmaceutically acceptable salt thereof.

9. The compound according to claim 6 wherein n is 0, a pharmaceutically acceptable salt thereof.

10. The compound according to any one of claim 3 or 6 wherein R$^2$ and R$^3$ are taken together with the adjacent carbon atom to form 6 membered cycloalkane, a pharmaceutically acceptable salt thereof.

11. The compound according to any one of claims 1, 3 and 6 wherein each of R$^2$ and R$^3$ is, same or different, C2-C3 alkyl, a pharmaceutically acceptable salt thereof.

12. The compound according to any one of claims 1, 3 and 6 wherein R$^4$ is methyl or ethyl, a pharmaceutically acceptable salt thereof.

13. A pharmaceutical composition which contains the compound according to any one of claims 1, 3 and 6, a pharmaceutically acceptable salt thereof as an active ingredient and a pharmaceutically acceptable carrier.

14. A method for treating pain which comprises administering the compound according to any one of claims 1, 3 and 6, a pharmaceutically acceptable salt thereof.

15. A method for treating pruritus which comprises administering the compound according to any one of claims 1, 3 and 6, a pharmaceutically acceptable salt thereof.

16. A method for treating bronchodilation which comprises administering the compound according to any one of claims 1, 3 and 6, a pharmaceutically acceptable salt thereof.

* * * * *